US007894994B2

(12) United States Patent
Hyde et al.

(10) Patent No.: US 7,894,994 B2
(45) Date of Patent: Feb. 22, 2011

(54) MULTIPHASIC CELLULAR REGULATION

(75) Inventors: Roderick A. Hyde, Livermore, CA (US); Muriel Y. Ishikawa, Livermore, CA (US); Edward K. Y. Jung, Bellevue, WA (US); Clarence T. Tegreene, Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 310 days.

(21) Appl. No.: 11/510,123

(22) Filed: Aug. 25, 2006

(65) Prior Publication Data

US 2008/0052004 A1    Feb. 28, 2008

(51) Int. Cl.
*G06F 19/00* (2006.01)
(52) U.S. Cl. .......................................... 702/19
(58) Field of Classification Search .................. None
See application file for complete search history.

(56) References Cited

PUBLICATIONS (Meyerson. Journal of Clinical Oncology (2000) vol. 18, No. 13, pp. 2626-2634).*
Bacchetti, Silvia; "Telomere dynamics and telomerase activity in cell senescence and cancer"; Seminars in Cell & Developmental Biology; Bearing a date of 1996; pp. 31-39; vol. 7; Academic Press Ltd.
Hahn, William C.; and Weinberg, Robert A.; "Modelling the Molecular Circuitry of Cancer"; Nature Reviews | Cancer; Bearing dates of 2002, and May 2002; pp. 331-341; vol. 2; Nature Publishing Group.
Kammori, Makoto; Nakamura, Ken-Ichi; Kanauchi, Hajime; Obara, Takao; Kawahara, Masaki; Mimura, Yoshikazu; Kaminishi, Michio; and Takubo, Kaiyo; "Consistent Decrease in Telomere Length in Parathyroid Tumors but Alteration in Telomerase Activity Limited to Malignancies: Preliminary Report"; World Journal of Surgery; Bearing dates of 2002, and Sep. 2002; pp. 1083-1087; vol. 26, No. 9; Société Internationale de Chirurgie.
Altucci, Lucia; Rossin, Aurelie; Raffelsberger, Wolfgang; Reitmair, Armin; Chomienne, Christine; Gronemeyer, Hinrich; "Retinoic Acid-Induced Apoptosis in Leukemia Cells is Mediated by Paracrine Action of Tumor-Selective Death Ligand TRAIL"; Nature Medicine; Jun. 2001 and also bearing dates of Dec. 4, 2000 and Apr. 9, 2001; pp. 680-686; vol. 7; No. 6; Nature Publishing Group.
Artandi, Steven E.; Chang, Sandy; Lee, Shwu-Luan; Alson, Scott; Gottlieb, Geoffrey J.; Chin, Lynda; DePhino, Ronald A.; "Telomere Dysfunction Promotes Non-Reciprocal Translocations and Epithelial Cancers in Mice"; Nature—Letters to Nature; Aug. 10, 2000; pp. 641-645; vol. 406; MacMillan Magazines Ltd.

Chen, Zhi, Koeneman, Kenneth S.; Corey, David R.; "Consequences of Telomerase Inhibition and Combination Treatments for the Proliferation of Cancer Cells"; Cancer Research; Sep. 15, 2003 and also bearing dates of Mar. 12, 2003, May 27, 2003, and Jun. 27, 2003; pp. 5917-5925; vol. 63; Departments of Pharmacology, Biochemistry and Urology of the University of Texas Southwestern Medical Center at Dallas, Texas.
Damm, Klaus; Hemmann, Ulrike; Garin-Chesa, Pilar; Hauel, Norbert; Kauffmann, Iris; Priepke, Henning; Niestroj, Claudia; Daiber, Christine; Enenkel, Barbara; Guilliard, Bernd; Lauritsch, Ines; Muller, Elfriede; Pascolo, Emanuelle; Sauter, Gabriele; Pantic, Milena; Martens, Uwe M.; Wenz, Christian; Lingner, Joachim; Kraut, Norbert; Rettig, Wolfgang J.; Schnapp, Andreas; "A Highly Selective Telomerase Inhibitor Limiting Human Cancer Cell Proliferation"; The EMBO Journal; 2001 and also bearing dates of Sep. 11, 2001, Oct. 23, 2001 and Oct. 26, 2001; pp. 6958-6968; vol. 20; No. 24; European Molecular Biology Organization.
Epel, Elissa S.; Blackburn, Elizabeth H. Lin, Jue; Dhabhar, Firdaus, S.; Adler, Nancy E.; Morrow, Jason D.; Cawthon, Richard M.; "Accelerated Telomere Shortening in Response to Life Stress"; PNAS—Psychology; Dec. 7, 2004 and also bearing a date of Sep. 28, 2004; pp. 17312-17315; vol. 101; No. 49; The National Academy of Sciences of the USA.
Gellert, Ginelle C.; Jackson, Shalmica R.; Dikmen, Z. Gunnur; Wright, Woodring E.; Shay, Jerry W.; "Telomerase as a Therapeutic Target in Cancer"; Elsevier Drug Discovery Today: Disease Mechanisms; bearing a date of 2005; pp. 159-164; vol. 2; No. 2; Elsevier Ltd.
Hanahan, Douglas; "Benefits of Bad Telomeres"; Nature—News and Views; Aug. 10, 2000; pp. 573-574; vol. 406; MacMillan Magazines Ltd.
Karhadkar, Sunil S.; Bova, G. Steven; Abdallah, Nadia; Dhara, Surajit; Gardner, Dale; Maitra, Anirban; Isaacs, John T.; Berman, David M.; Beachy, Philip A.; "Hedgehog Signalling in Prostate Regeneration, Neoplasia and Metastasis"; Nature—Letters to Nature; Jul. 9, 2004; pp. 1-5; vol. 2962; Nature Publishing Group.
Salomoni, Paolo; Pandolfi, Pier Paolo; "Transcriptional Regulation of Cellular Transformation"; Nature Medicine—News & Views; Jul. 2000; pp. 742-744; vol. 6; No. 7; Nature America Inc.
Sanchez, Pilar; Hernandez, Ana Maria; Stecca, Barbara; Kahler, Andrea J.; DeGueme, Amy M.; Barrett, Andrea; Beyna, Mercedes; Datta, Milton W.; Datta, Sumana; Altaba, Ariel Ruiz I; "Inhibition of Prostate Cancer Proliferation by Interference with Sonic Hedgehog-GLI1 Signaling"; PNAS—Developmental Biology; Aug. 24, 2004 and also bearing dates of Mar. 23, 2004 and Jun. 26, 2004; pp. 12561-12566; vol. 101; No. 34; The National Academy of Sciences of the USA.

(Continued)

*Primary Examiner*—Lori A Clow

(57) ABSTRACT

Methods and systems are described that relate to multiphasic cellular regulation. Methods and systems include accepting input identifying target cell populations, accepting input identifying at least one specified alteration in metabolic activity and accepting input identifying at least one specified alteration in telomerase activity.

40 Claims, 27 Drawing Sheets

OTHER PUBLICATIONS

Shay; Jerry W.; Wright, Woodring E.; "Mechanism-Based Combination Telomerase Inhibition Therapy"; Cancer Cell—Previews; Jan. 2005; vol. 7; Elsevier Inc.

Wang, Zengquan; Boudjelal, Mohamed; Kang, Sewon; Voorhees, John J.; Fisher, Gary J.; Ultraviolet Irradiation of Human Skin Causes Functional Vitamin A Deficiency, Preventable by All-Trans Retinoic Acid Pre-Treatment; Nature Medicine—Articles; April 1999 and also bearing dates of Dec. 14, 1998 and Feb. 4, 1999; pp. 418-422; vol. 5; No. 4; Nature America Inc.

Wong, W. Wei-Lynn; Tan, Melissa M.; Xia, Zhenlei; Dimitroulakos, Jim; Minden, Mark D.; Penn, Linda Z.; "Cerivastatin Triggers Tumor-Specific Apoptosis With Higher Efficacy Than Lovastatin"; Clinical Cancer Research; Jul. 2001 and also bearing dates of Dec. 28, 2000 and Apr. 20, 2001; pp. 2067-2075; vol. 7; Ontario Cancer Institute.

Calvi, L.M.; Adams, G.B.; Weibrecht, K.W.; Weber, J.M.; Olson, D.P.; Knight, M.C.; Martin, R.P.; Schipani, E.; Divieti, P.; Bringhurst, F.R.; Milner, L.A.; Kronenberg, H.M.; and Scadden, D.T.; "Osteoblastic cells regulate the haematopoietic stem cell niche"; Nature; Oct. 23, 2003; pp. 841-846; vol. 425; Nature Publishing Group.

Check, Erika; "The rocky road to success"; Nature; Sep. 8, 2005; pp. 185-186; vol. 437; Nature Publishing Group.

Cowan, Chad A.; Atienza, Jocelyn; Melton, Douglas A.; and Eggan, Kevin; "Nuclear Reprogramming of Somatic Cells After Fusion with Human Embryonic Stem Cells"; Science; Aug. 26, 2005; pp. 1369-1373; vol. 309.

D'Amour, Kevin A.; and Gage, Fred H.; "Genetic and functional differences between multipotent neural and pluripotent embryonic stem cells"; PNAS; Sep. 30, 2003; pp. 11866-11872; vol. 100, Suppl. 1; The National Academy of Sciences of the USA.

Dor, Yuval; Brown, Juliana; Martinez, Olga I.; and Melton, Douglas A.; "Adult pancreatic β-cells are formed by self-duplication rather than stem-cell differentiation"; Nature; May 6, 2004; pp. 41-46; vol. 429; Nature Publishing Group.

Haylock, David N.; and Nilsson, Susan K.; "Stem Cell Regulation by the Hematopoietic Stem Cell Niche"; Cell Cycle; Bearing dates of Jul. 25, 2005, Jul. 27, 2005, and Oct. 2005; pp. 1353-1355; vol. 4:10; Landes Bioscience.

Hurtley, Stella; and Szuromi, Phil; "This Week in Science, Stem Cell Research sans Embryos?"; Science; Aug. 26, 2005; pp. 1297-1298; vol. 309; AAAS.

Lemischka, Ihor R.; and Moore, Kateri A.; "Interactive niches"; Nature; Oct. 23, 2003; pp. 778-779; vol. 425.

Mikkers, Harald; and Frisén, Jonas; "New EMBO Member's Review, Deconstructing sternness"; The EMBO Journal; Bearing dates of 2005, May 9, 2005, Jun. 24, 2005, and Jul. 21, 2005; pp. 2715-2719; vol. 24; European Molecular Biology Organization.

Moore, Kateri A.; and Lemischka, Ihor R.; "'Tie-ing' down the Hematopoietic Niche"; Cell; Jul. 23, 2004; pp. 139-143; vol. 118; Cell Press.

Orkin, Stuart H.; "Chipping away at the Embryonic Stem Cell Network"; Cell; Sep. 2005; pp. 828-830.

Rasmussen, Theodore P; "Embryonic stem cell differentiation: A chromatin perspective"; Reproductive Biology and Endocrinology; Bearing dates of Jul. 14, 2003, Nov. 13, 2003, and Nov. 13, 2003; pp. 1-7; vol. 1:100; Rasmussen, licensee BioMed Central Ltd.; located at http://www.rbej.com/content/1/1/100.

Sharkis, Saul J.; "Canadian Stem Cell Scientists Take the Prize"; Cell; Sep. 23, 2005; pp. 817-819; vol. 122; Elsevier Inc.

Shaywitz, David A.; and Melton, Douglas A.; "The Molecular Biography of the Cell"; Cell; Mar. 25, 2005; pp. 729-731; vol. 120; Elsevier Inc.

Suárez-Fariñas, Mayte; Noggle, Scott; Heke, Michael; Hemmati-Brivanlou, Ali; and Magnasco, Marcelo O; "Comparing independent microarray studies: the case of human embryonic stem cells"; BMC Genomics; Bearing dates of Apr. 26, 2005 and Jul. 22, 2005; pp. 1-11; vol. 6:99; Suarez-Farinas et al, licensee BioMed Central Ltd.

Zaret, Ken; "Self-help for insulin cells"; Nature; May 6, 2004; pp. 30-31; vol. 429; Nature Publishing Group.

Zhang, Jiwang; Niu, Chao; Ye, Ling; Huang, Haiyang; He, Xi; Tong, Wei-Gang; Ross, Jason; Haug, Jeff; Johnson, Teri; Feng, Jian Q.; Harris, Stephen; Wiedemann, Leanne M.; Mishina, Yuji; and Li, Linheng; "Identification of the haematopoiectic stem cell niche and control of the niche size"; Nature; Oct. 23, 2003; pp. 836-841; vol. 425; Nature Publishing Group.

Cowan, Chad A.; Atienza, Jocelyn; Melton, Douglas A.; and Eggan, Kevin; "Supporting Online Material"; Science; bearing a date of Aug. 26, 2005; printed on Jan. 16, 2009; pp. 16-24 plus 5 pages (contains cover pages, Materials and Methods, Figs. S1 to S3, Tables S1 to S4, References and Notes); vol. 309.

* cited by examiner

MULTIPHASIC CELLULAR REGULATION

TECHNICAL FIELD

Methods and systems described herein involve computer operations related to multiphasic cellular regulation.

SUMMARY

In one aspect, a method includes but is not limited to: accepting input identifying a target cell population; accepting input identifying at least one specified alteration in metabolic activity in at least a part of the target cell population; and accepting input identifying at least one specified alteration in telomerase activity in at least a part of the target cell population. In addition to the foregoing, other method aspects are described in the claims, drawings, and text forming a part of the present disclosure.

In one aspect, a system includes but is not limited to a signal-bearing medium, bearing one or more instructions including: one or more instructions for accepting input identifying a target cell population; one or more instructions for accepting input identifying at least one specified alteration in metabolic activity in at least a part of the target cell population; and one or more instructions for accepting input identifying at least one specified alteration in telomerase activity in at least a part of the target cell population. In one aspect, a system includes but is not limited to circuitry for accepting input identifying a target cell population, circuitry for accepting input identifying at least one specified alteration in metabolic activity in at least a part of the target cell population, and circuitry for accepting input identifying at least one specified alteration in telomerase activity in at least a part of the target cell population. In one aspect, a system includes but is not limited to a means for accepting input identifying a target cell population, a means for accepting input identifying at least one specified alteration in metabolic activity in at least a part of the target cell population, and a means for accepting input identifying at least one specified alteration in telomerase activity in at least a part of the target cell population.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and/or system and/or program product aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
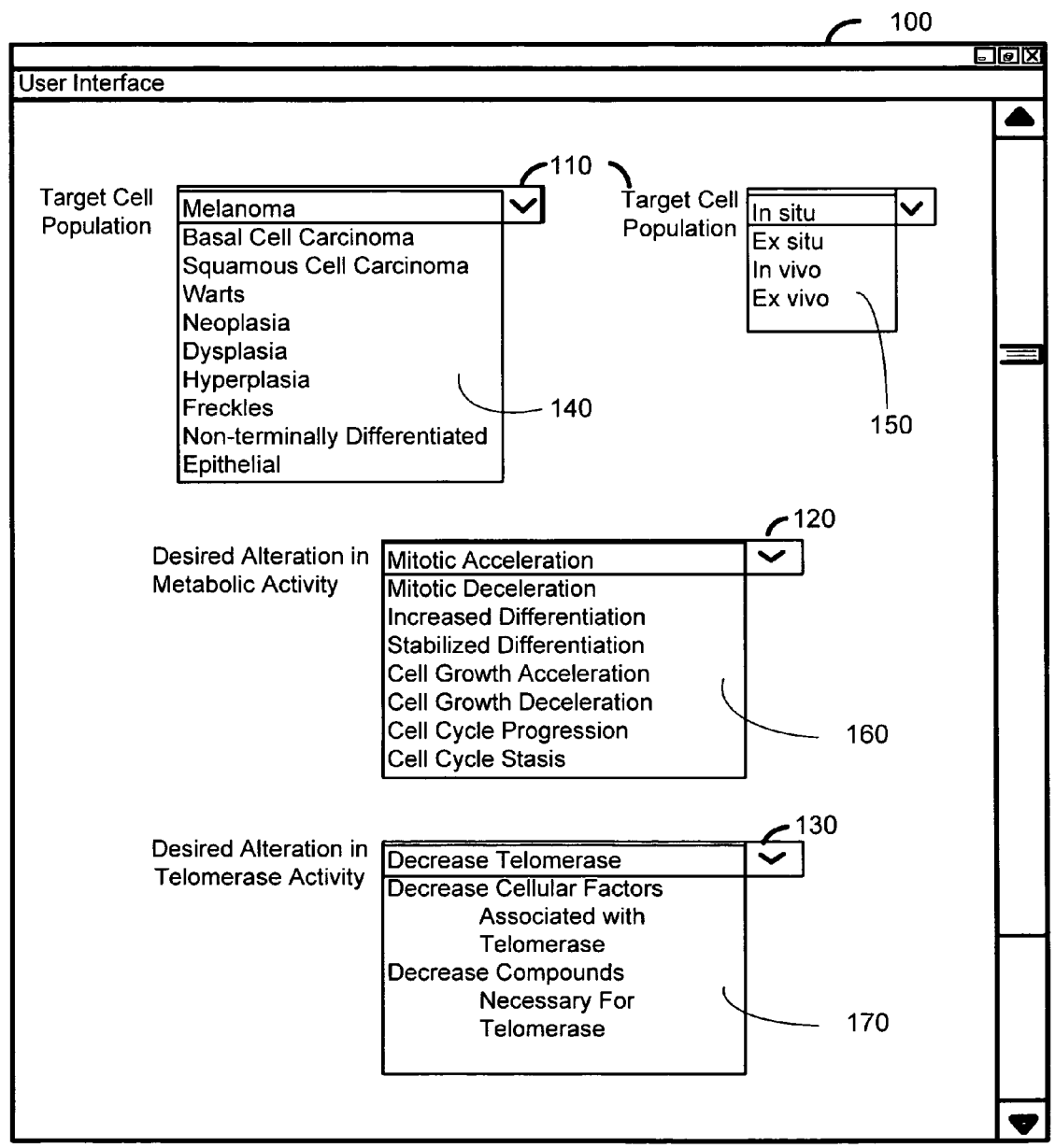
FIG. 1 is a schematic of an example user interface that illustrates some potential embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example user interface 100. A user interface 100 such as that shown may be, for example, part of a desktop computer system, a laptop computer system, a networked computer system and/or a handheld device such as a personal digital assistant (PDA). A user interface may include pull-down menus such as 110, 120, or 130, including input options such as examples 140, 150, 160, and 170. A user interface may include regions for a user to input data from, for example, a keyboard, touch-sensitive screen, or voice recognition system. In one aspect, a user interface 100 illustrates a mechanism for accepting input identifying a target cell population. For example, a pull down menu for accepting input identifying a target cell population 110 may include input options 140 for accepting input identifying at least one melanoma cell, basal cell carcinoma cell, squamous cell carcinoma cell, wart cell, neoplastic cell, dysplastic cell, hyperplastic cell, freckle cell, non-terminally differentiated cell, or epithelial cell. As a further example, a user interface for accepting input identifying a target cell population 110 may include input options 150 for accepting input identifying a target cell population in situ, ex situ, in vivo, or ex vivo.

In one aspect, a user interface 100 may illustrate a mechanism for accepting input identifying at least one specified alteration in metabolic activity in at least a part of the target cell population. Alterations in metabolic activity may include pull-down menu terms in the user interface 100 such as "decrease in cell growth" or "increase in functional p53 levels" or "increase in apoptosis". For example, a user interface 100 for accepting input identifying at least one specified alteration in metabolic activity in at least a part of the target cell population may include a pull-down menu 120 including input options 160 for accepting input identifying mitotic acceleration, mitotic deceleration, increased differentiation, stabilized differentiation, cell growth acceleration, cell growth deceleration, cell cycle progression, or cell cycle stasis.

In one aspect, a user interface 100 may illustrate a mechanism for accepting input identifying at least one specified alteration in telomerase activity in at least a part of the target cell population. Accepting input identifying at least one specified alteration in telomerase activity may include pull-down menu terms in the user interface 100 such as "decrease in telomerase activity" or "reduction in telomerase RNA component (TERC) levels" or "reduction in telomerase reverse transcriptase (TERT) levels". For example, user interface 100 for accepting input identifying at least one specified alteration in telomerase activity in at least a part of the target cell population may include a pull-down menu 130 including input options 170 for accepting input identifying decrease in telomerase, decrease in cellular factors associated with telomerase, or decrease in compounds necessary for telomerase.

Figure 2:
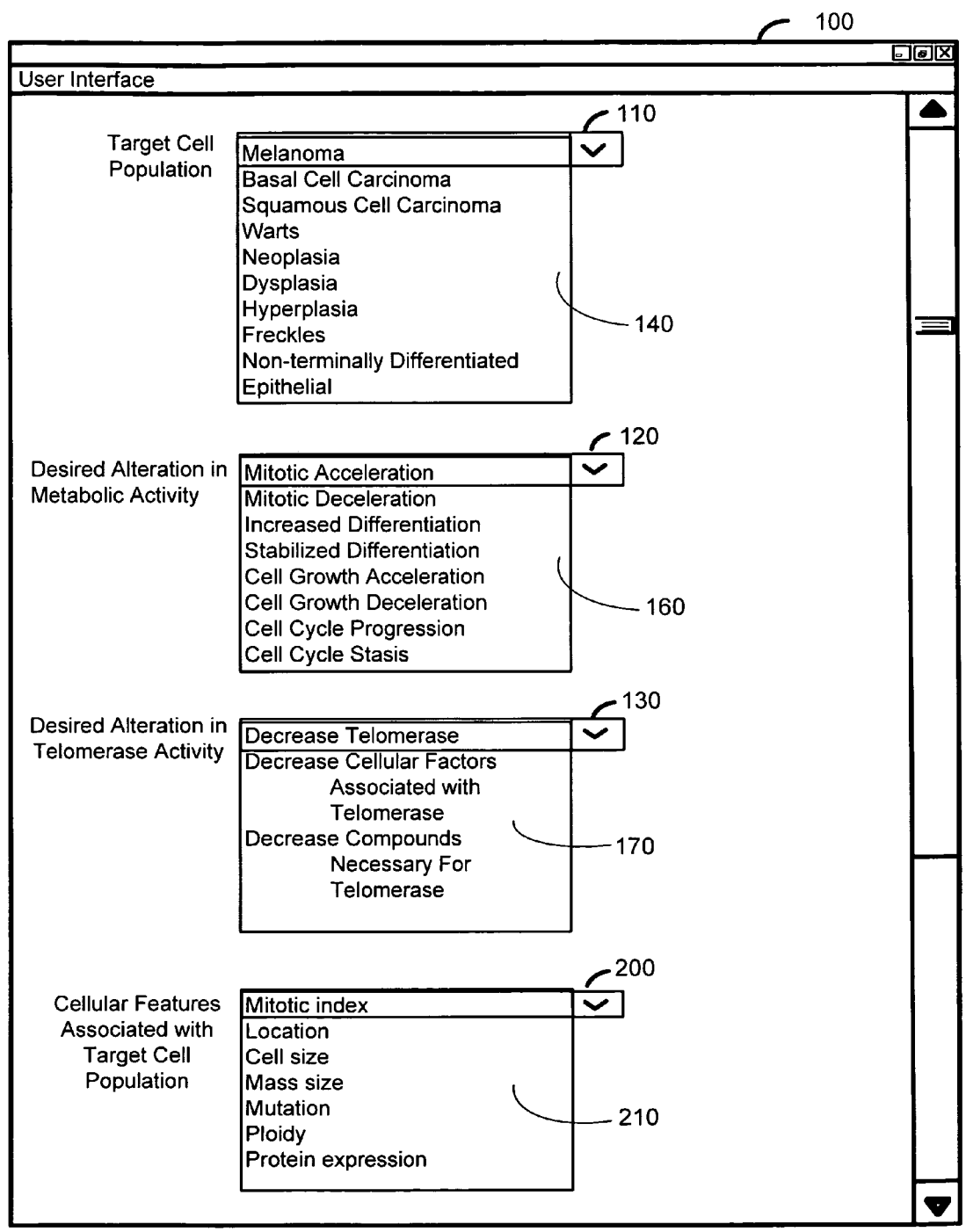
FIG. 2 illustrates a further example user interface.

FIG. 2 illustrates further aspects of user interface 100. As an example, user interface 100 may include a pull-down menu 110 for accepting input identifying a target cell population, a pull-down menu 120 for accepting input identifying at least one specified alteration in metabolic activity in at least a part of the target cell population and a pull-down menu 130 for accepting input identifying at least one specified alteration in telomerase activity in at least a part of the target cell population. User interface 100 may also include a pull-down menu 200 for accepting input identifying one or more cellular features associated with the target cell population. Pull-down menu 200 for accepting input identifying one or more cellular features associated with the target cell population may, for example, include terms such as "facial skin" or "aneuploid" or "HER-2/NEU protein hyperexpression". For example, pull-down menu 200 for accepting input identifying one or more cellular features associated with the target cell population may include input options 210 for accepting input identifying mitotic index, location, cell size, mass size, mutation, ploidy, or protein expression.

Figure 3:
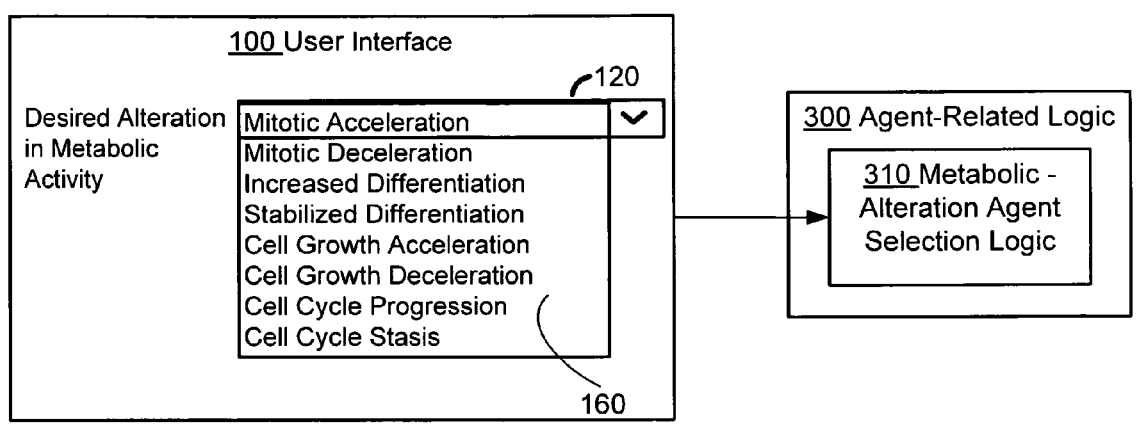
FIG. 3 is a schematic of some aspects of the methods and systems described herein.
Figure 4:
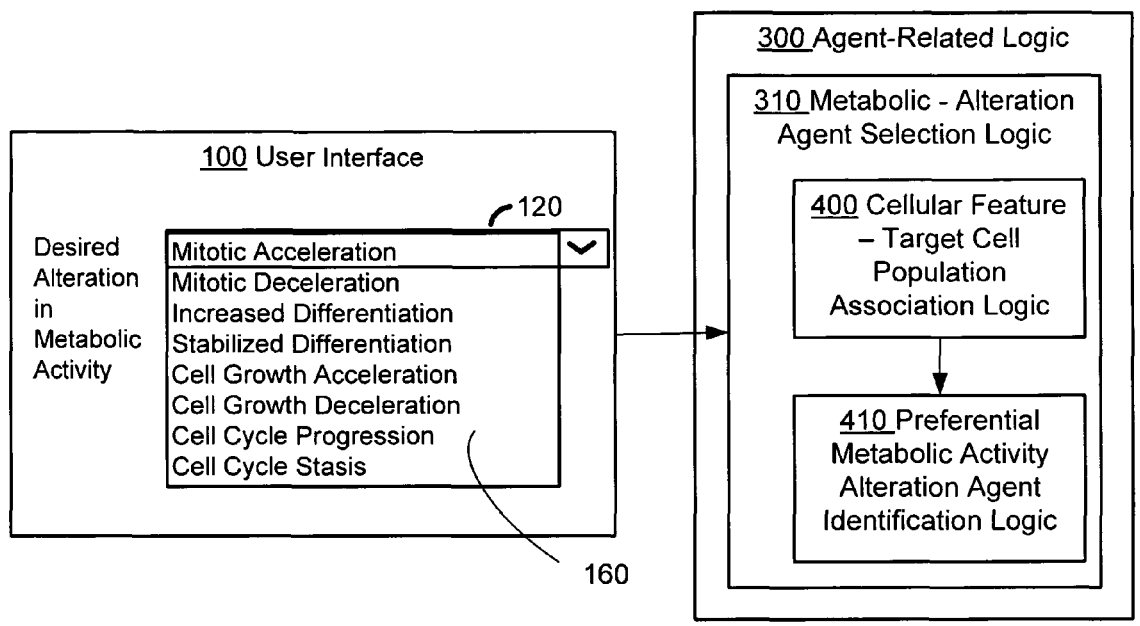
FIG. 4 is a schematic of some aspects of the methods and systems described herein.

FIG. 3 is a schematic illustrating aspects of the methods and systems described herein. Methods and systems include those involving "logic". As used herein, logic may include hardware, software, firmware and any combinations thereof. Embodiments may include agent-related logic 300, including metabolic-alteration agent selection logic 310. For example, some embodiments of agent-related logic 300 include metabolic-alteration agent selection logic 310, selecting at least one metabolic-alteration agent in response to the desired alteration in metabolic activity in the at least the part of the target cell population. Further potential aspects of agent-related logic 300 and metabolic-alteration agent selection logic 310 are illustrated in FIG. 4. In some embodiments, metabolic-alteration agent selection logic 310 includes cellular feature-target cell population association logic 400 and may also include preferential metabolic activity alteration agent identification logic 410. Cellular feature-target cell population association logic 400 may include known associations that exist between at least one cell in a target cell population and potential cellular features. Cellular feature-target cell population association logic 400 may include logic for recalling one or more cellular feature characteristics associated with the target cell population. Preferential metabolic activity alteration agent identification logic 410 may include logic for identifying at least one agent predicted to preferentially alter metabolic activity in response to the one or more cellular feature characteristics associated with the target cell population.

Figure 5:
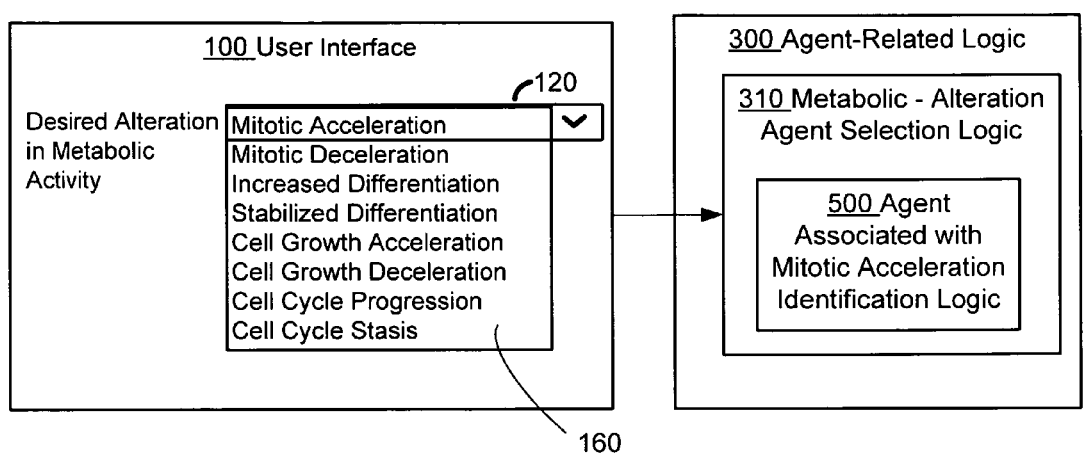
FIG. 5 is a schematic of some aspects of the methods and systems described herein.

As shown in FIG. 5, agent-related logic 300 and metabolic-alteration agent selection logic 310 may also include agent associated with mitotic acceleration identification logic 500. In some aspects, mitotic acceleration identification logic 500 includes logic for identifying at least one agent associated with mitotic acceleration. For example, mitotic acceleration identification logic 500 may identify a specific agent or class of agents associated with mitotic acceleration in a given embodiment.

Figure 6:
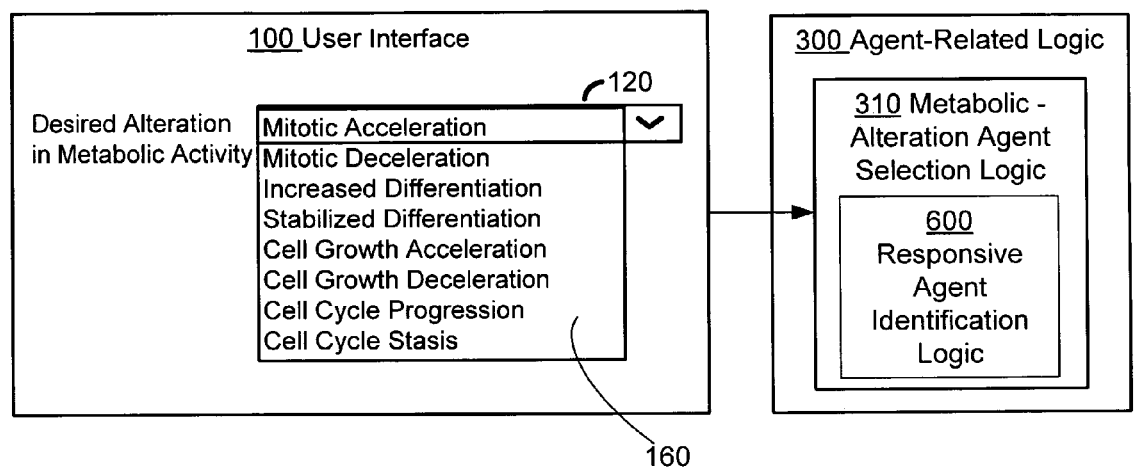
FIG. 6 is a schematic of some aspects of the methods and systems described herein.

FIG. 6 illustrates that agent related logic 300 may include metabolic-alteration agent selection logic 310 which may further include responsive agent identification logic 600. Responsive agent identification logic 600 may include logic for identifying at least one metabolic-alteration agent in response to a desired alteration in metabolic activity related to differentiation, mitosis, cell growth, or cell cycle activity.

Figure 7:
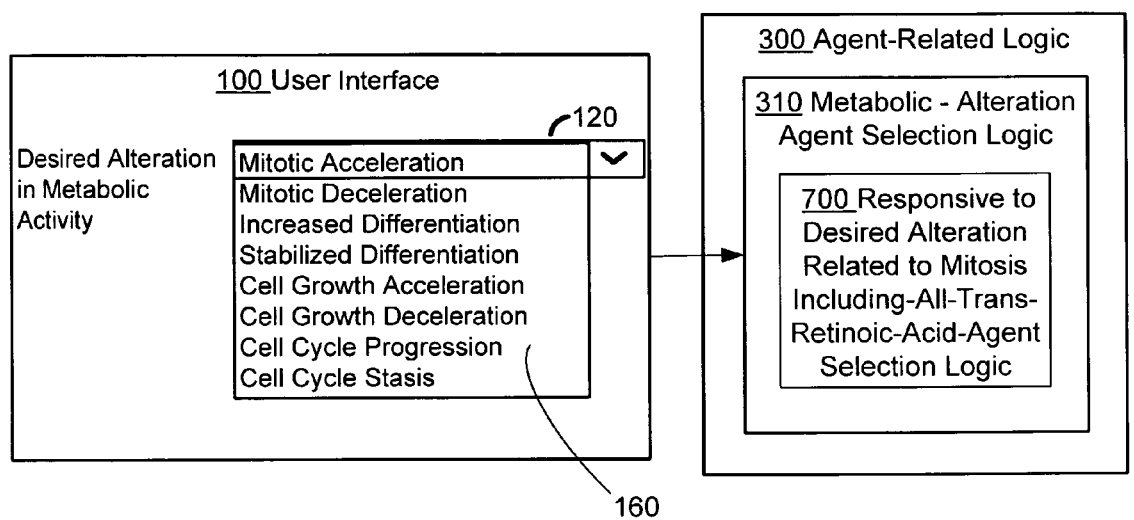
FIG. 7 is a schematic of some aspects of the methods and systems described herein.

FIG. 7 illustrates that agent related logic 300 may include metabolic-alteration agent selection logic 310 which may further include responsive to desired alteration related to mitosis including-all-trans-retinoic-acid-agent selection logic 700. Responsive to desired alteration related to mitosis including-all-trans-retinoic-acid-agent selection logic 700 may include logic for identifying at least one agent that includes all trans retinoic acid in response to a desired alteration in metabolic activity related to mitosis.

Figure 8:
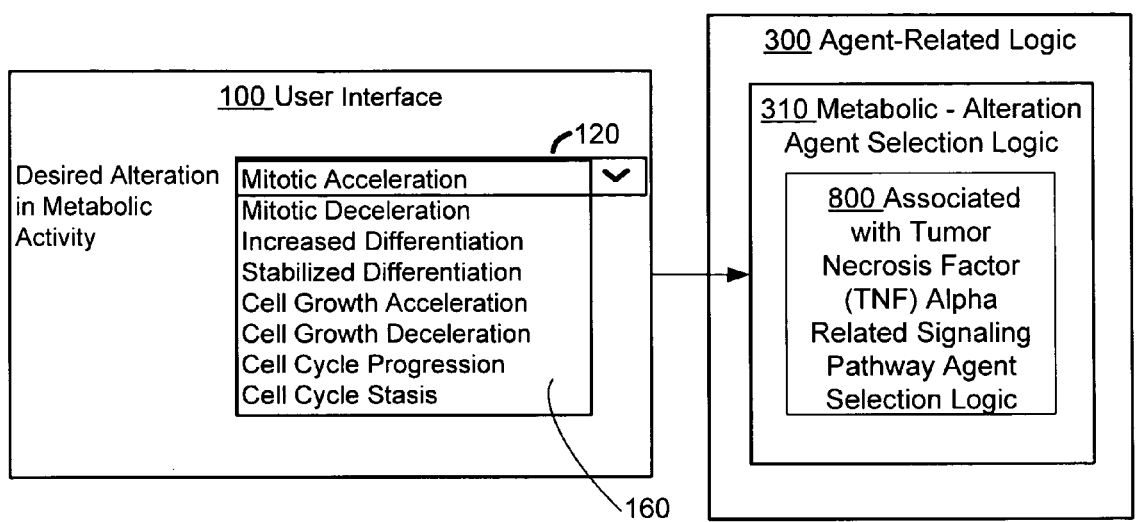
FIG. 8 is a schematic of some aspects of the methods and systems described herein.

FIG. 8 illustrates that agent related logic 300 may include metabolic-alteration agent selection logic 310 which may further include associated with tumor necrosis factor (TNF) alpha related signaling pathway agent selection logic 800. Associated with tumor necrosis factor (TNF) alpha related signaling pathway agent selection logic 800 may include logic for identifying at least one agent associated with a tumor necrosis factor (TNF) alpha related signaling pathway.

Figure 9:
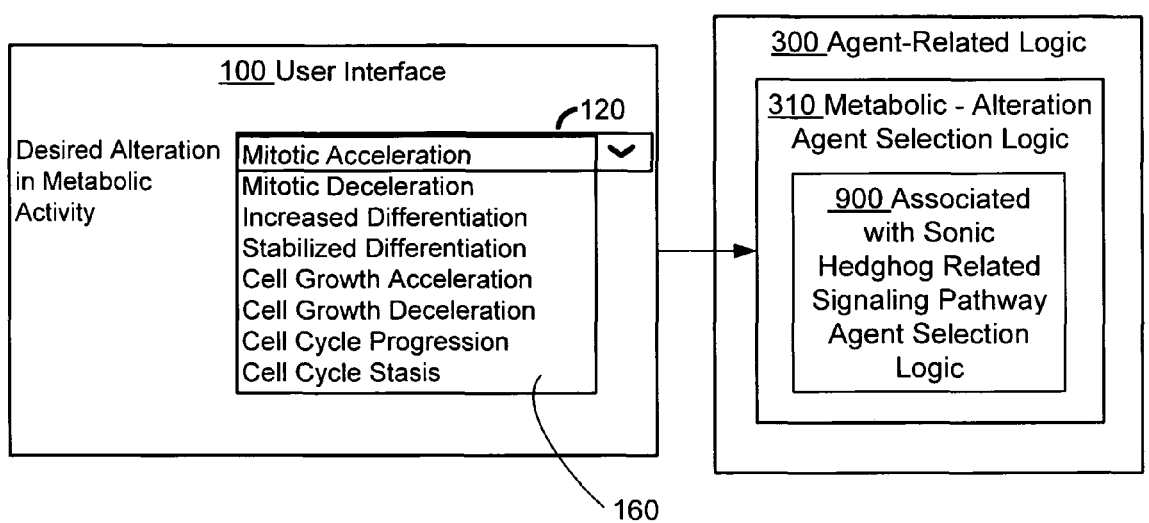
FIG. 9 is a schematic of some aspects of the methods and systems described herein.

FIG. 9 illustrates that agent related logic 300 may include metabolic-alteration agent selection logic 310 which may further include associated with Sonic Hedgehog related signaling pathway agent selection logic 900. Associated with Sonic Hedgehog related signaling pathway agent selection logic 900 may include logic for identifying at least one agent associated with a Sonic Hedgehog related signaling pathway. For example, logic for identifying at least one agent associated with a Sonic Hedgehog related signaling pathway may include logic for identifying a class of agents, or may also include logic for identifying at least one specific agent.

Figure 10:
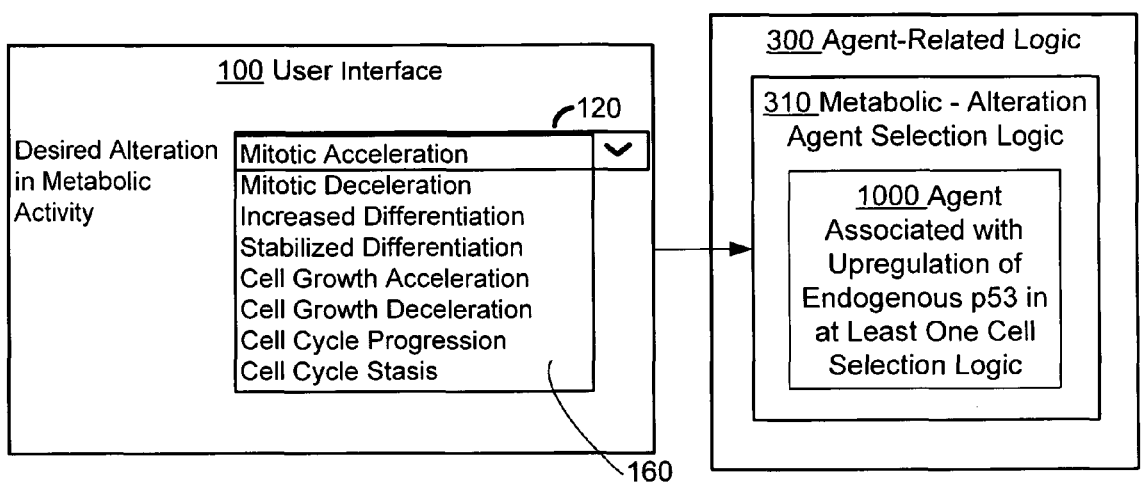
FIG. 10 is a schematic of some aspects of the methods and systems described herein.

FIG. 10 illustrates that agent related logic 300 may include metabolic-alteration agent selection logic 310 which may further include agent associated with upregulation of endogenous p53 in at least one cell selection logic 1000. Agent associated with upregulation of endogenous p53 in at least one cell selection logic 1000 may include logic for identifying at least one agent associated with upregulation of endogenous p53 in at least one cell.

Figure 11:
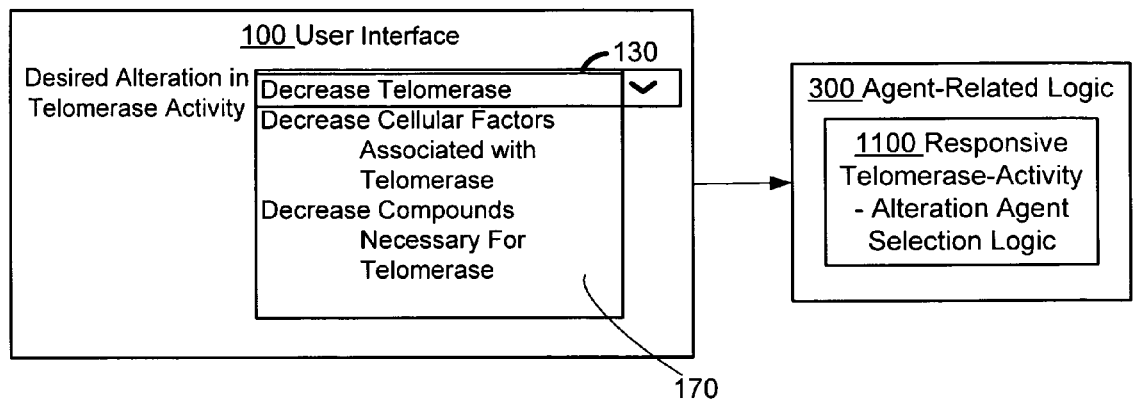
FIG. 11 is a schematic of some aspects of the methods and systems described herein.

The agent-related logic 300 may also include responsive telomerase-activity-alteration agent selection logic 1100 as illustrated in FIG. 11. Responsive telomerase-activity-alteration agent selection logic 1100 may include logic for selecting at least one telomerase-activity-alteration agent in response to the desired alteration in telomerase activity in the at least the part of the target cell population. Responsive telomerase-activity-alteration agent selection logic 1100 may further include logic for selecting at least one telomerase-activity-alteration agent in response to a desired decrease in telomerase activity, decrease in activity of one or more cellular factors associated with telomerase or decrease in activity of one or more compounds required for telomerase activity. For example, if the desired alteration in telomerase activity is a decrease in telomerase, the responsive telomerase-activity-alteration agent selection logic 1100 may select one or more of: a decrease in the telomerase complex, a decrease in proteins included in the telomerase complex, and/or a decrease in nucleotides included in the telomerase complex.

Figure 12:
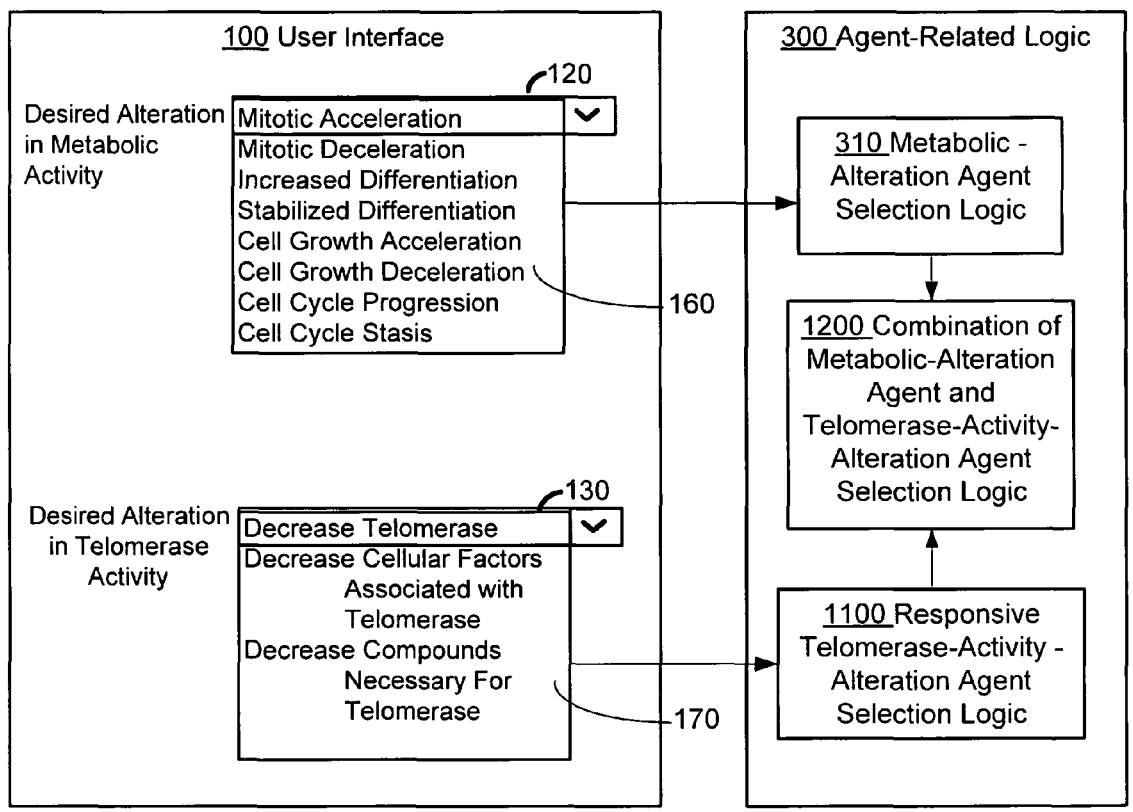
FIG. 12 is a schematic of some aspects of the methods and systems described herein.
Figure 13:
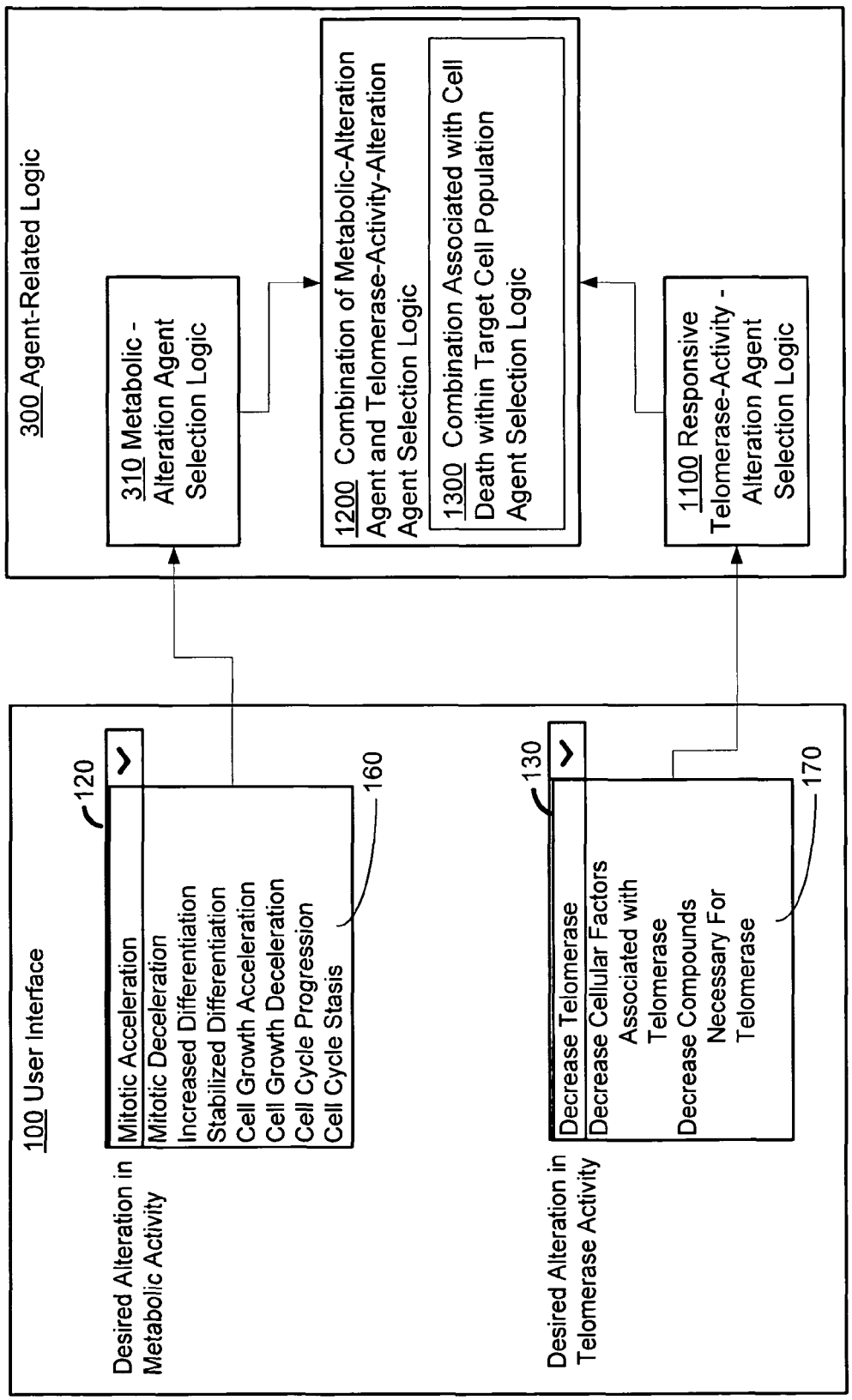
FIG. 13 is a schematic of some aspects of the methods and systems described herein.

Methods and systems described herein may include selecting at least one metabolic-alteration agent in response to the desired alteration in metabolic activity in the at least the part of the target cell population, selecting at least one telomerase-activity-alteration agent in response to the desired alteration in telomerase activity in the at least the part of the target cell population, and selecting at least one combination of at least one said metabolic-alteration agent and at least one said telomerase-activity-alteration agent. As shown in FIG. 12, agent related logic 300 may include metabolic-alteration agent selection logic 310, responsive telomerase-activity-alteration agent selection logic 1100 and combination of metabolic-alteration agent and telomerase-activity-alteration agent selection logic 1200. As illustrated in FIG. 13, combination of metabolic-alteration agent and telomerase-activity-alteration agent selection logic 1200 may further include combination associated with cell death within target cell population agent selection logic 1300.

Figure 14:
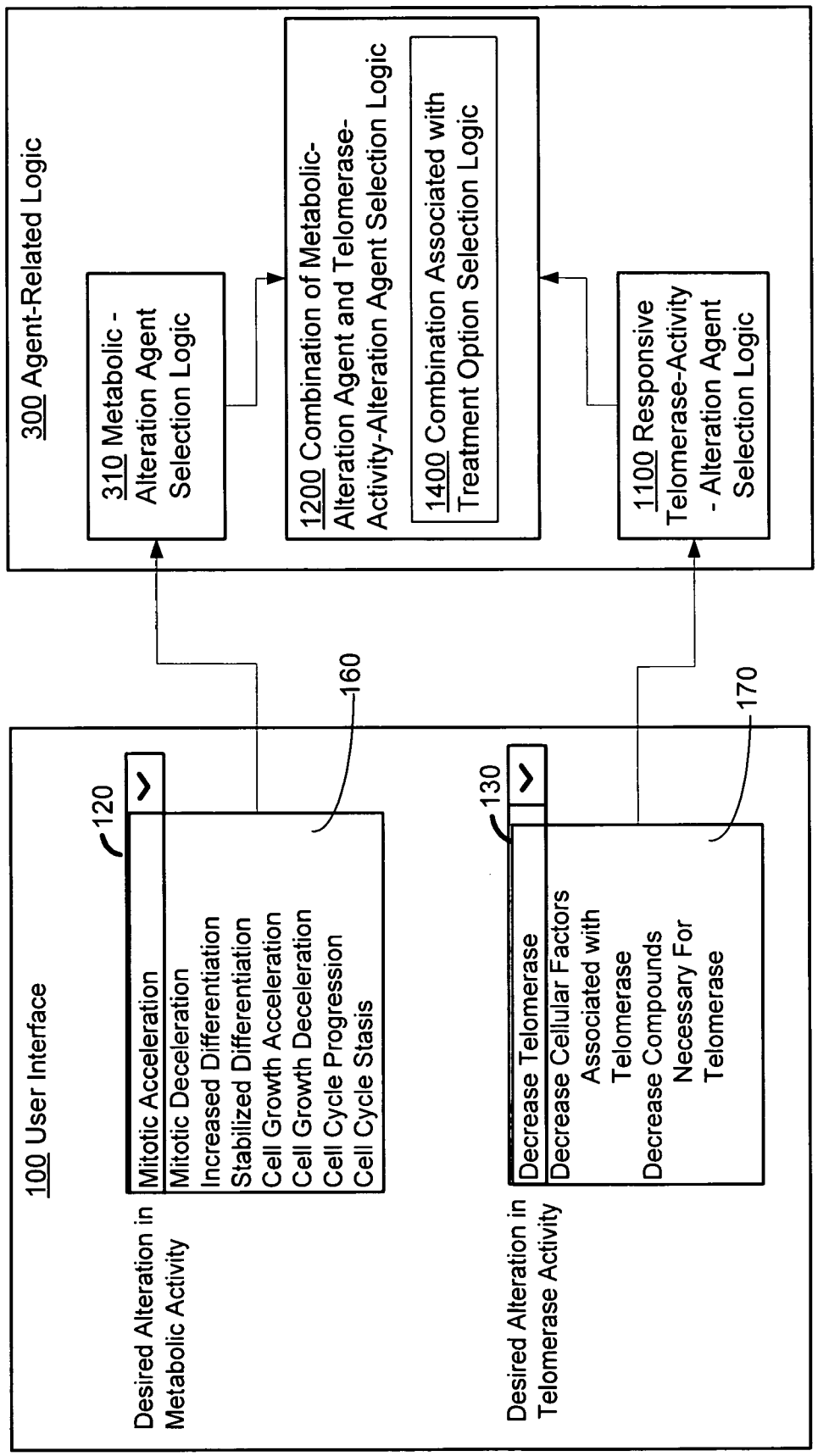
FIG. 14 is a schematic of some aspects of the methods and systems described herein.
Figure 15:
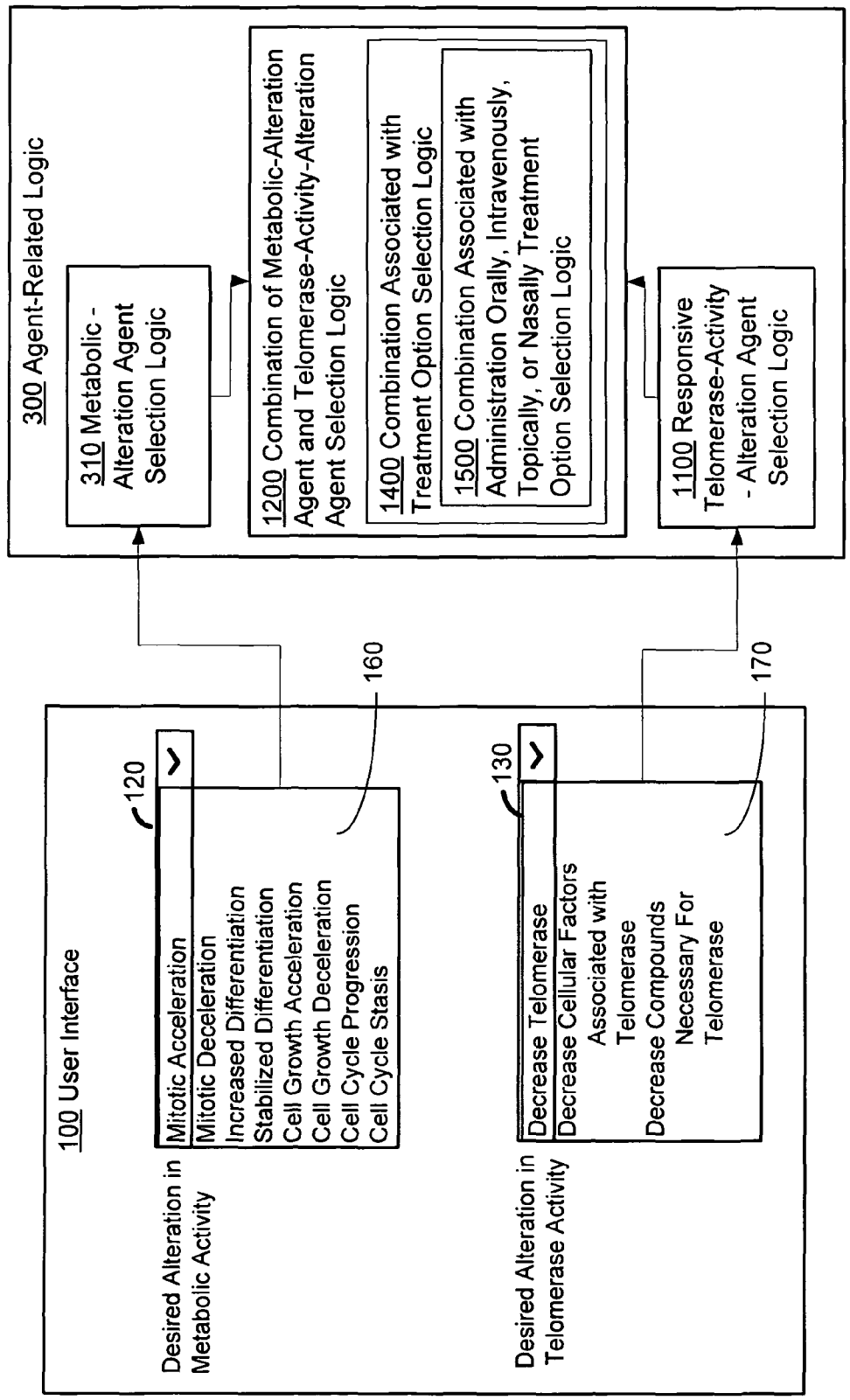
FIG. 15 is a schematic of some aspects of the methods and systems described herein.
Figure 16:
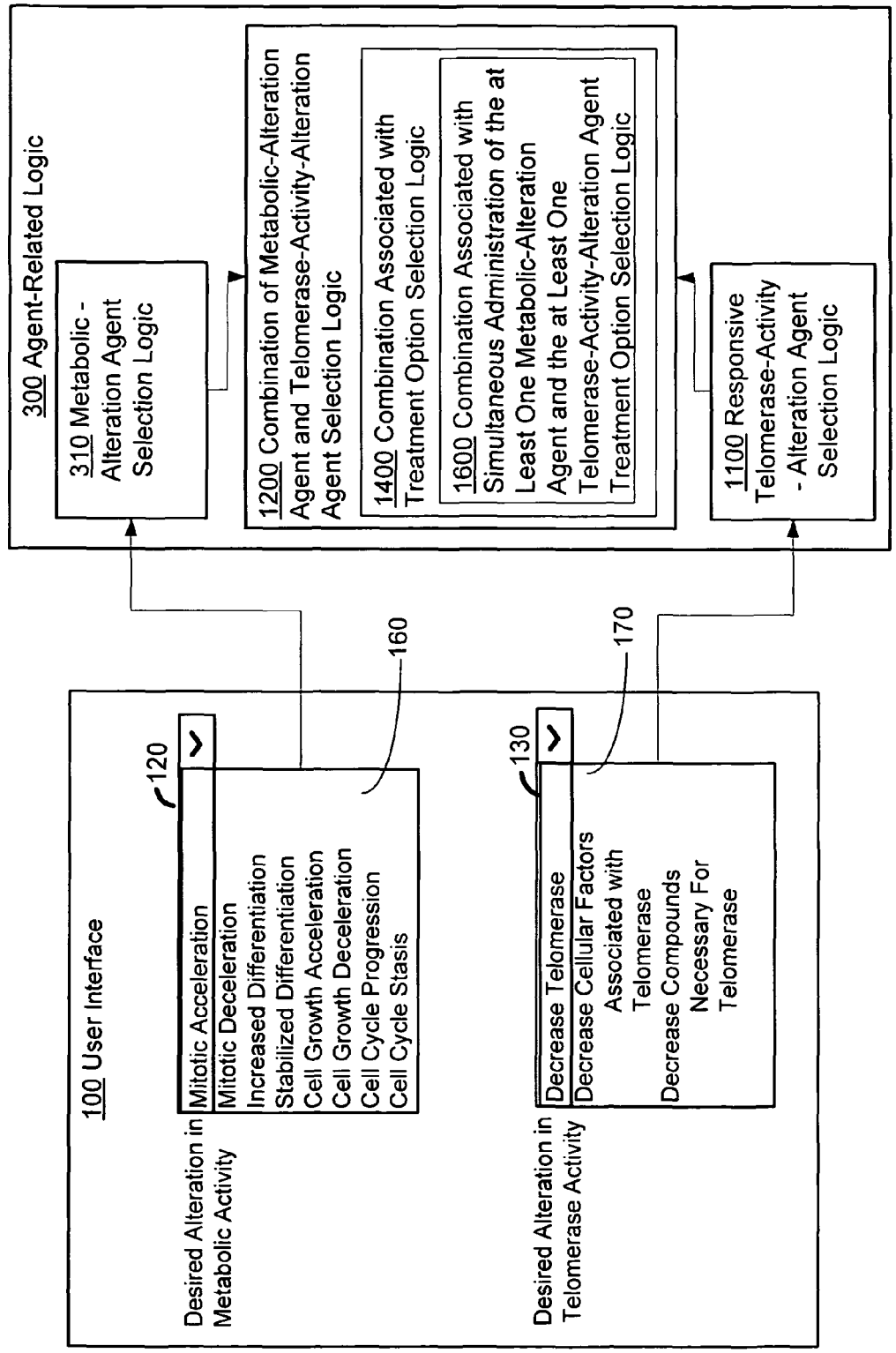
FIG. 16 is a schematic of some aspects of the methods and systems described herein.
Figure 17:
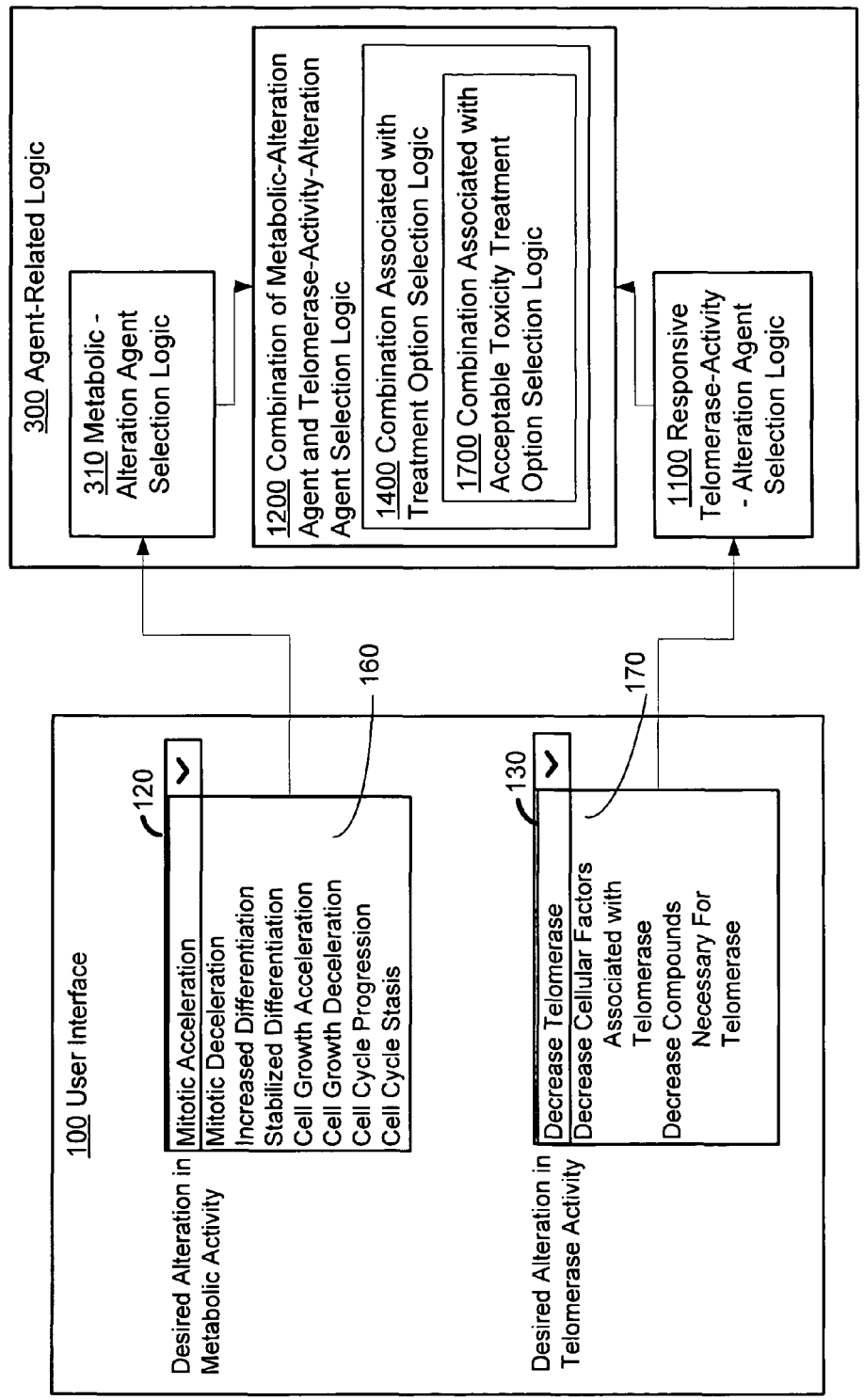
FIG. 17 is a schematic of some aspects of the methods and systems described herein.

Methods and systems described herein further include those wherein combination of metabolic-alteration agent and telomerase-activity-alteration agent selection logic 1200 may include combination associated with treatment option selection logic 1400, as illustrated in FIG. 14. As illustrated in FIG. 15, combination of metabolic-alteration agent and telomerase-activity-alteration agent selection logic 1200 may include combination associated with treatment option selection logic 1400 and may further include combination associated with administration orally, intravenously, topically, or nasally treatment option selection logic 1500. As illustrated in FIG. 16, combination of metabolic-alteration agent and telomerase-activity-alteration agent selection logic 1200 may include combination associated with treatment option selection logic 1400 and may further include combination associated with simultaneous administration of the at least one metabolic-alteration agent and the at least one telomerase-activity-alteration agent treatment option selection logic 1600. As illustrated in FIG. 17, combination of metabolic-alteration agent and telomerase-activity-alteration agent selection logic 1200 may include combination associated with treatment option selection logic 1400 and may include combination associated with acceptable toxicity treatment option selection logic 1700.

Figure 18:
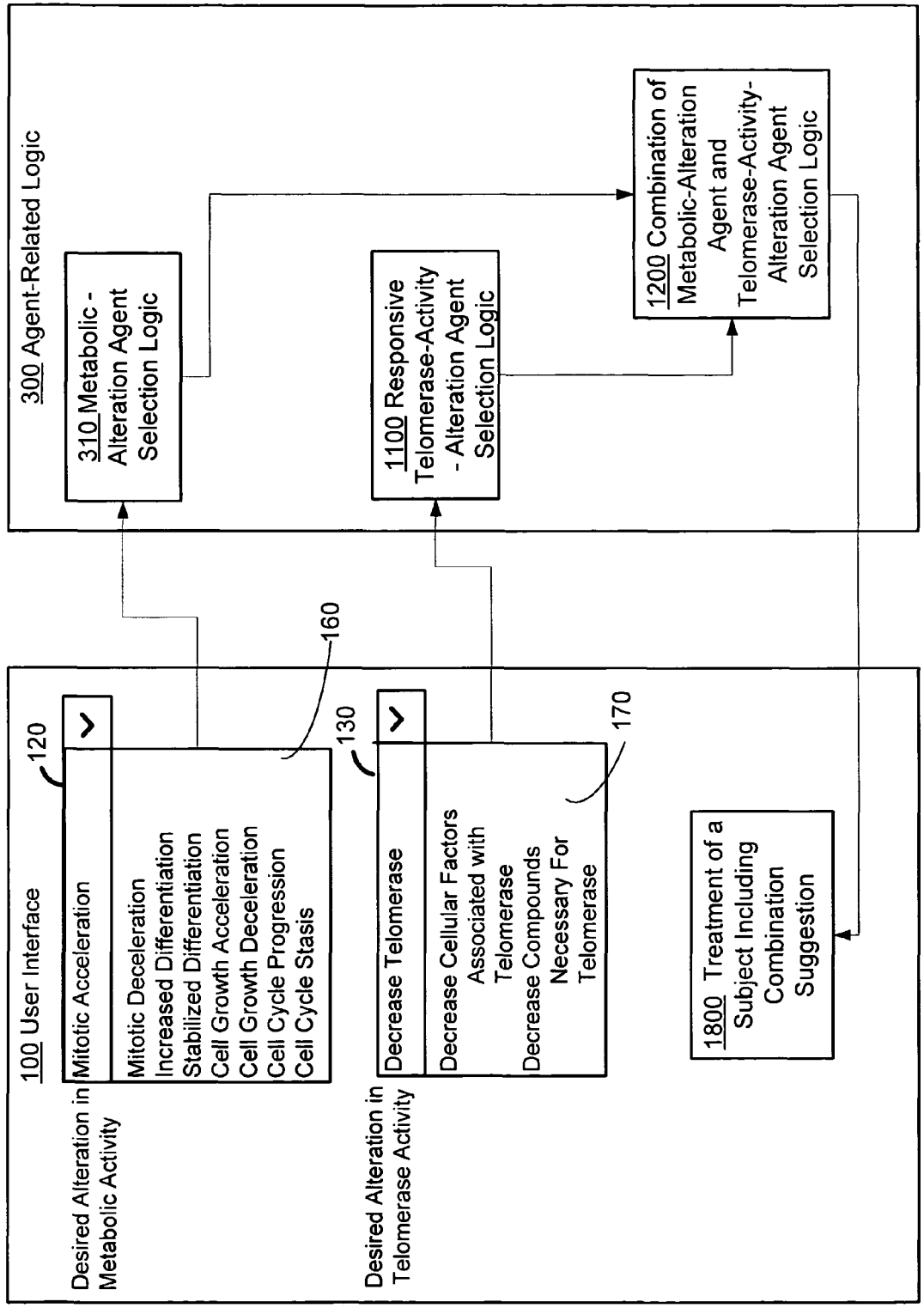
FIG. 18 is a schematic of some aspects of the methods and systems described herein.

In some embodiments, selecting at least one combination of at least one said metabolic-alteration agent and at least one said telomerase-activity-alteration agent may include suggesting treatment of at least one subject including the combination. As illustrated in FIG. 18, the combination of metabolic-alteration agent and telomerase-activity-alteration agent selection logic 1200 may be operably linked to a treatment of a subject including combination suggestion user interface 1800. A treatment of a subject including combination suggestion user interface 1800 may be, for example, included in the same user interface as pull-down menus such as that shown in user interface 100 in FIG. 18, or combination suggestion user interface 1800 may be a distinct interface. In some embodiments, a user interface for accepting input such as those labeled 110, 120 and 130 in FIGS. 1 through 18 and a combination suggestion user interface 1800 may be directed towards different users, with associated distinct embodiments in, for example, hardware, software or firmware.

Figure 19:
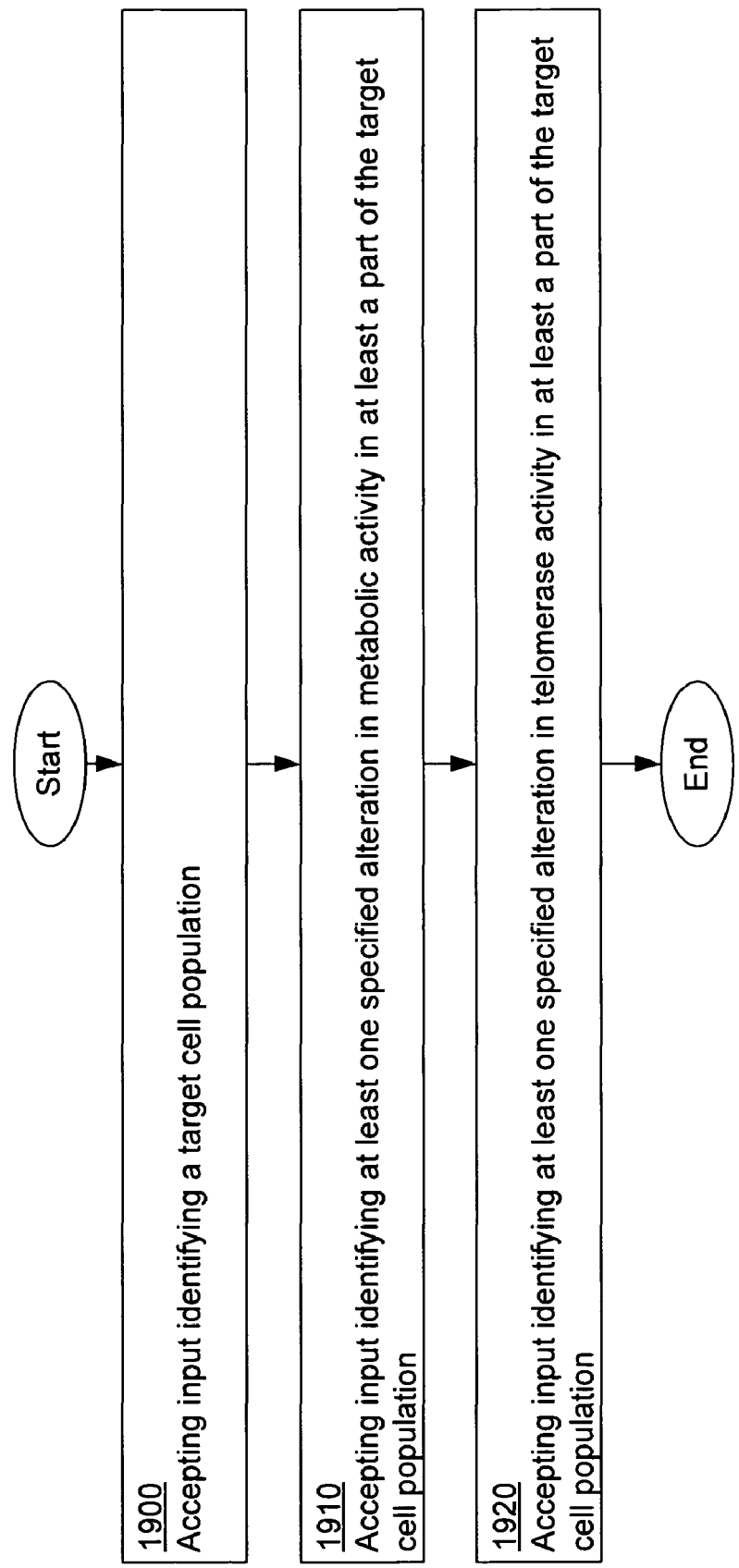
FIG. 19 is a flowchart illustrating embodiments of the methods and systems described herein.

FIG. 19 illustrates aspects of a system representing examples of operations that are related to the methods and systems described herein. In FIG. 19 and in following figures that include various examples of operations, discussion and explanation may be provided with respect to the above-described examples of FIGS. 1 through 18, and/or with respect to other examples and contexts. However, it should be understood that the operations may be executed in a number of other environments and contexts, and/or modified versions of FIGS. 1 through 18. Also, although the various operations are presented in the sequence(s) illustrated, it should be understood that the various operations may be implemented in other orders than those which are illustrated, or may be implemented concurrently.

FIG. 19 illustrates a high level logic flowchart of a process. Operational block 1900 shows accepting input identifying a target cell population. In one implementation, accepting input identifying a target cell population includes the use of a user interface such as, for example, a keyboard, stylus, personal digital assistant (PDA) and/or pull-down menus. Illustrative pull-down menus for accepting input identifying a target cell population are shown, for example, in FIG. 1 and FIG. 2, labeled as 110. A target cell population may include, for example, at least one melanoma cell, basal cell carcinoma cell, squamous cell carcinoma cell, wart cell, neoplastic cell, dysplastic cell, hyperplastic cell, freckle cell, non-terminally differentiated cell, or epithelial cell. The target cell population may include at least one population of cells identifiable by one or more parameters such as cell location, cell type, cellular activity, cellular proteins, cell morphology, genomic status, or cell cycle status. For example, the target cell population may include cells in situ, ex situ, in vivo or ex vivo.

Operational block 1910 depicts accepting input identifying at least one specified alteration in metabolic activity in at least a part of the target cell population. In one implementation, accepting input identifying at least one specified alteration in metabolic activity in at least a part of the target cell population includes the use of a user interface such as, for example, a keyboard, stylus, personal digital assistant (PDA) and/or pull-down menus. Illustrative pull-down menus for accepting input identifying at least one specified alteration in metabolic activity in at least a part of the target cell population are shown, for example, in FIGS. 1 through 10 and FIGS. 12 through 18, labeled as 120. An alteration in metabolic activity may include, for example, mitotic acceleration, mitotic deceleration, increased differentiation, stabilized differentiation, cell growth acceleration, cell growth deceleration, cell cycle progression, or cell cycle stasis.

Operational block 1920 illustrates accepting input identifying at least one specified alteration in telomerase activity in at least a part of the target cell population. In one implementation, accepting input identifying at least one specified alteration in telomerase activity in at least a part of the target cell population includes the use of a user interface such as, for example, a keyboard, stylus, personal digital assistant (PDA) and/or pull-down menus. Illustrative pull-down menus for accepting input identifying at least one specified alteration in telomerase activity in at least a part of the target cell population are shown in FIGS. 1, 2 and 11 through 18 labeled as 130. An alteration in telomerase activity may include, for example, decrease in telomerase activity, decrease in activity of one or more cellular factors associated with telomerase or decrease in activity of one or more compounds required for telomerase activity. In some embodiments, an alteration in telomerase activity may include, for example, increase in telomerase activity, increase in activity of one or more cellular factors associated with telomerase or increase in activity of one or more compounds required for telomerase activity.

Input for these operations may be accepted through user interfaces such as those described above, or by other user interfaces as desired in a given embodiment.

Figure 20:
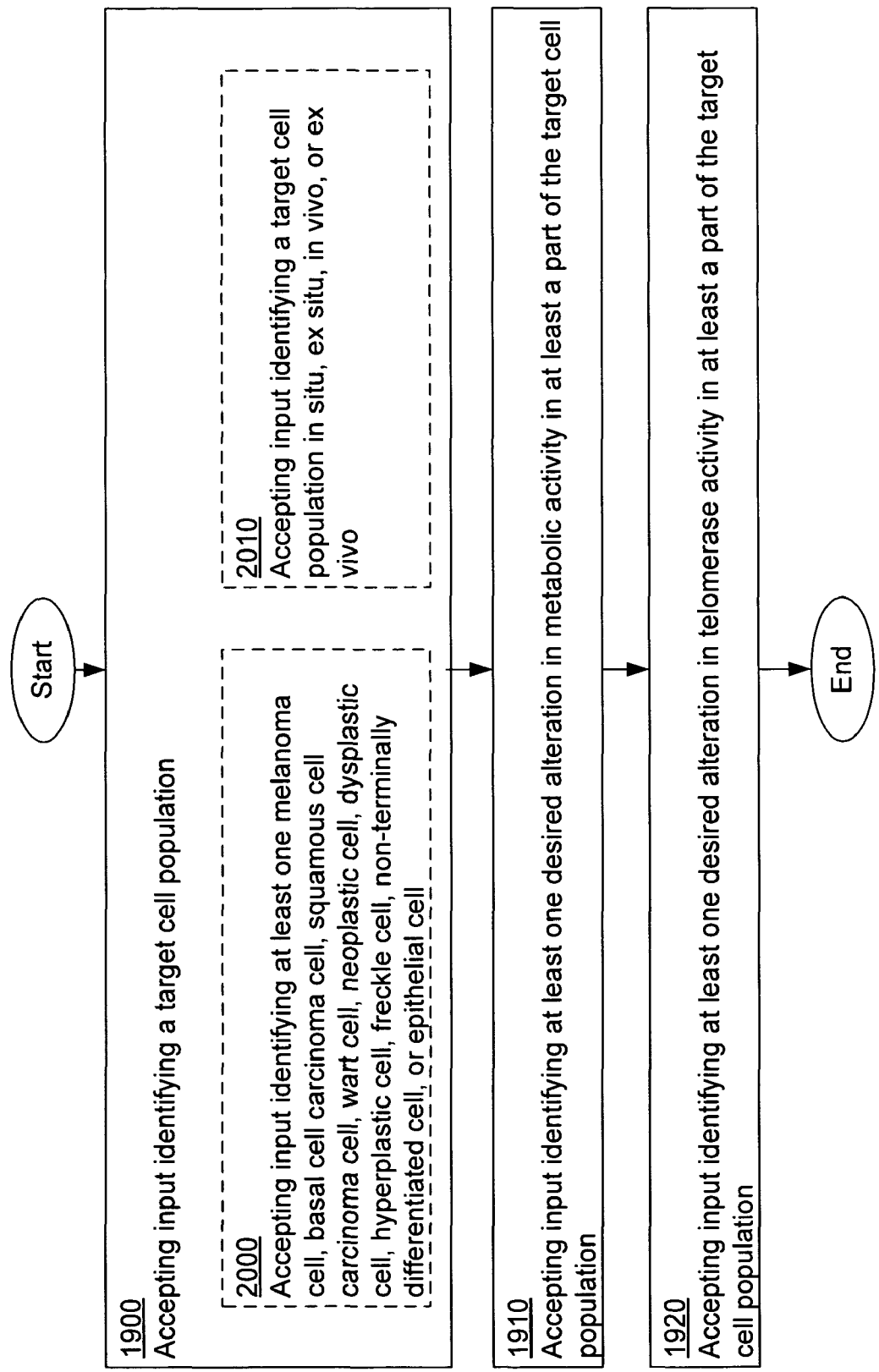
FIG. 20 is a flowchart illustrating further aspects of embodiments of the methods and systems described herein.

FIG. 20 shows one or more alternate implementations of the high level logic flowchart of FIG. 19. Operational block 2000 depicts that accepting input identifying a target cell population 1900 may include accepting input identifying at least one melanoma cell, basal cell carcinoma cell, squamous cell carcinoma cell, wart cell, neoplastic cell, dysplastic cell, hyperplastic cell, freckle cell, non-terminally differentiated cell, or epithelial cell. Operational block 2010 depicts that accepting input identifying a target cell population 1900 may include accepting input identifying a target cell population in situ, ex situ, in vivo, or ex vivo. In one implementation, a target cell population is defined by location relative to the body of an organism, but it may also be defined by other parameters such as, for example, expression of cell surface proteins, expression of cell surface carbohydrates, morphology, pathology, or cell response to external agents. A target cell population may include a homogeneous population of cells or a heterogeneous population of cells. A target cell population may include two or more cells and may, in some embodiments, include progeny cells.

Figure 21:
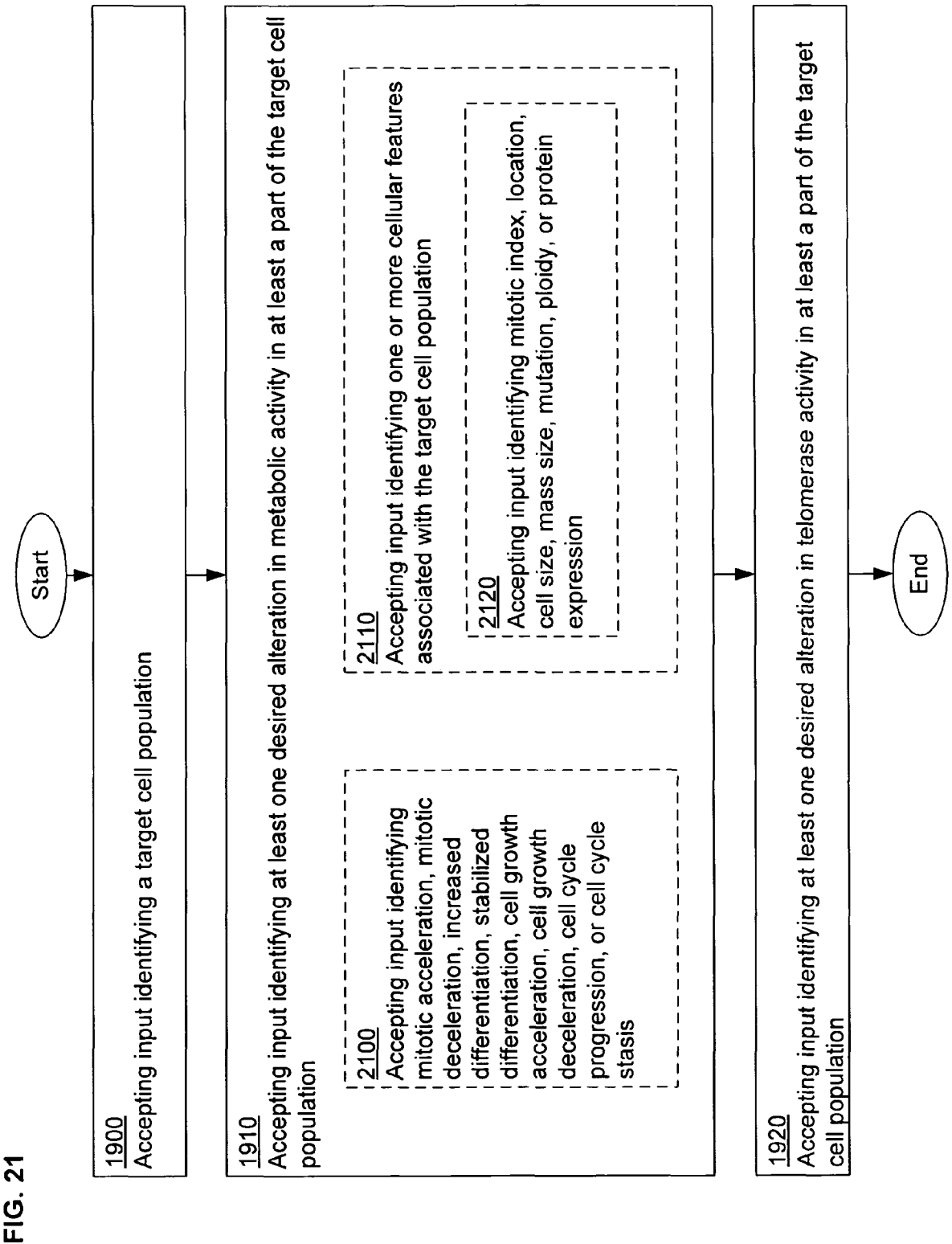
FIG. 21 is a flowchart illustrating further aspects of embodiments of the methods and systems described herein.

As illustrated in FIG. 21, one or more instructions for accepting input identifying at least one specified alteration in metabolic activity in at least a part of the target cell population 1910 may further include accepting input identifying mitotic acceleration, mitotic deceleration, increased differentiation, stabilized differentiation, cell growth acceleration, cell growth deceleration, cell cycle progression, or cell cycle stasis 2100. In one aspect, accepting input identifying at least one specified alteration in metabolic activity in at least a part of the target cell population 1910 may also include accepting input identifying one or more cellular features associated with the target cell population 2110, which may further include accepting input identifying mitotic index, location, cell size, mass size, mutation, ploidy, or protein expression 2120.

Figure 22:
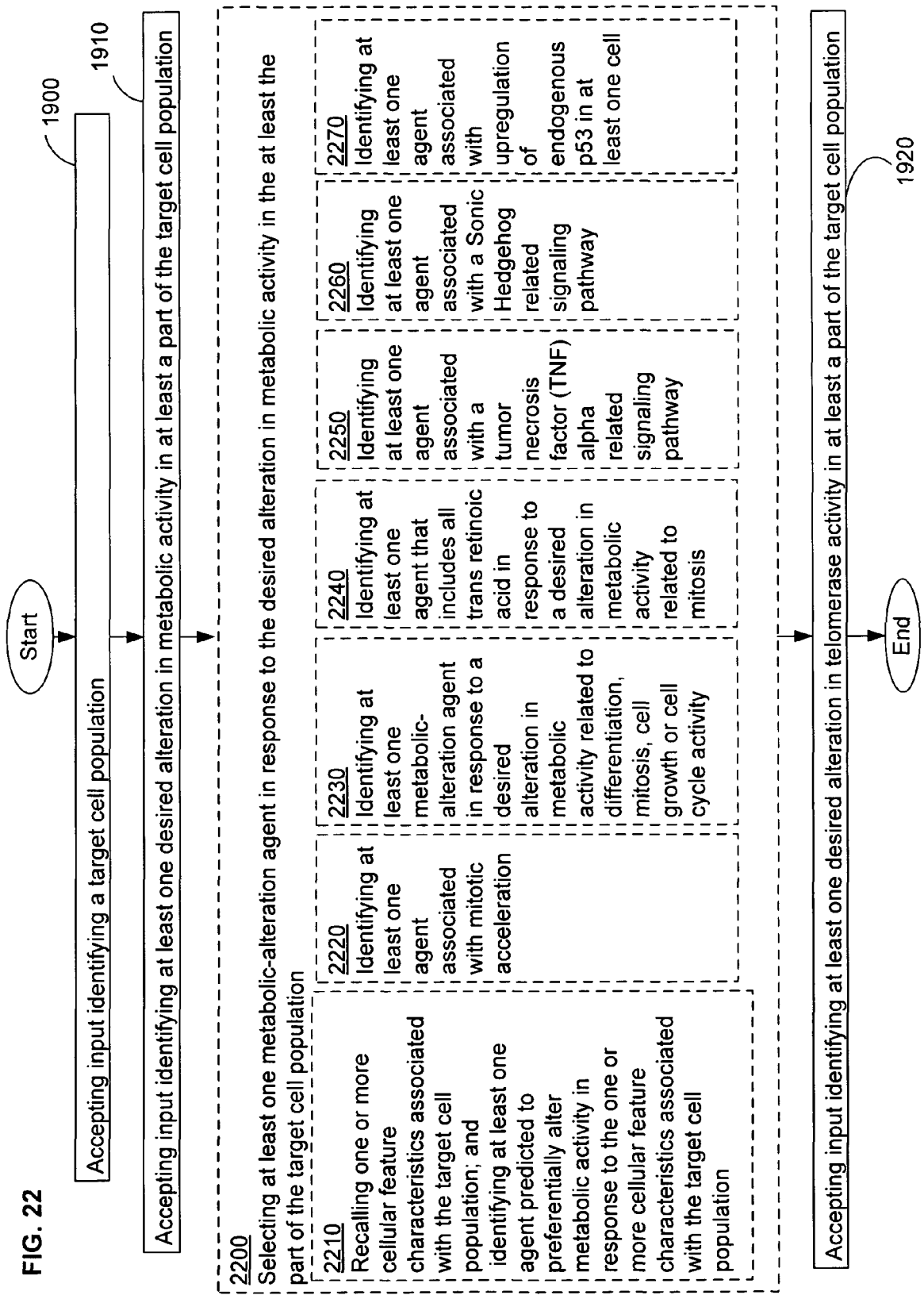
FIG. 22 is a flowchart illustrating further aspects of embodiments of the methods and systems described herein.

As illustrated in FIG. 22, methods and systems may also include selecting at least one metabolic-alteration agent in response to the desired alteration in metabolic activity in the at least the part of the target cell population 2200. In one aspect, selecting at least one metabolic-alteration agent in response to the desired alteration in metabolic activity in the at least the part of the target cell population 2200 may further include recalling one or more cellular feature characteristics associated with the target cell population; and identifying at least one agent predicted to preferentially alter metabolic activity in response to the one or more cellular feature characteristics associated with the target cell population 2210. For example, if the target cell population includes at least one breast carcinoma cell, an associated cellular feature may be expression of estrogen receptor protein (e.g. ER+/ER−), and the at least one agent predicted to preferentially alter metabolic activity may include tamoxifen and/or anastrozole. For example, if the target cell population includes at least one epithelial cell, an associated cellular feature may be ionic transport pore structures, such as serum sodium (e.g. Na+) channels, and the at least one agent predicted to preferentially alter metabolic activity may include amiloride, benzamil, and/or triamterene.

In one aspect, selecting at least one combination of at least one said metabolic-alteration agent and at least one said telomerase-activity-alteration agent 2200 may further include identifying at least one agent associated with mitotic acceleration 2220. For example, agents may include caffeine, norreticuline, steroids, maturation promoting factor (MPF), and related compounds. Agents may further be associated with mitotic acceleration in a specified cell or tissue type.

In one aspect, selecting at least one metabolic-alteration agent in response to the desired alteration in metabolic activity in the at least the part of the target cell population 2200 may also include identifying at least one metabolic-alteration agent in response to a desired alteration in metabolic activity related to differentiation, mitosis, cell growth, or cell cycle activity 2230. A metabolic-alteration agent identified may include a specific: agent or class of agents; drug, or class of drugs; compound, or class of compounds. For example, if the desired alteration in metabolic activity is increased differentiation, at least one metabolic-alteration agent identified may be: phosphonate 9-(2-phosphonyl-methoxyethyl)adenine (PMEA); arsenic trioxide; valproic acid; differentiation agents as a class or group; hormones; and/or steroids.

In one aspect, selecting at least one metabolic-alteration agent in response to the desired alteration in metabolic activity in the at least the part of the target cell population 2200 may include identifying at least one agent that includes all trans retinoic acid in response to a desired alteration in metabolic activity related to mitosis 2240. For example, identifying at least one agent that includes all trans retinoic acid in response to a desired alteration in metabolic activity related to mitosis 2240 may, depending on the embodiment, include identifying tretinoin, vesamoid or related compounds.

In one aspect, selecting at least one metabolic-alteration agent in response to the desired alteration in metabolic activity in the at least the part of the target cell population 2200 may include identifying at least one agent associated with a tumor necrosis factor (TNF) alpha related signaling pathway 2250. For example, depending on the embodiment, identifying at least one agent associated with a tumor necrosis factor (TNF) alpha related signaling pathway 2250 may include identifying: a class or group of TNF alpha-inhibitors; a class or group of TNF alpha-promoters; or specific compounds such as remicade, infliximab, humira, adalimumab, etanercept, enbrel, thalidomide, and/or CDP870.

In one aspect, selecting at least one metabolic-alteration agent in response to the desired alteration in metabolic activity in the at least the part of the target cell population 2200 may include identifying at least one agent associated with a Sonic Hedgehog related signaling pathway 2260. For example, identifying at least one agent associated with a Sonic Hedgehog related signaling pathway 2260 may include identifying agents such as cyclopamine; HhAntag-691; AY9944; jervine; purmorphamine; tomatidine; SANT-1; and/or U1866A.

In one aspect, selecting at least one metabolic-alteration agent in response to the desired alteration in metabolic activity in the at least the part of the target cell population 2200 may include identifying at least one agent associated with upregulation of endogenous p53 in at least one cell 2270. As used herein, upregulation of endogenous p53 may be achieved by mechanisms known to those of skill in the art, including, for example, by drugs, exposure to radiation, increased availability of an active form of p53, or through increased expression of the p53 gene. For example, identifying at least one agent associated with upregulation of endogenous p53 in at least one cell may include identifying drugs such as cisplatin, methotrexate, or ethylnitrosourea (ENU).

Figure 23:
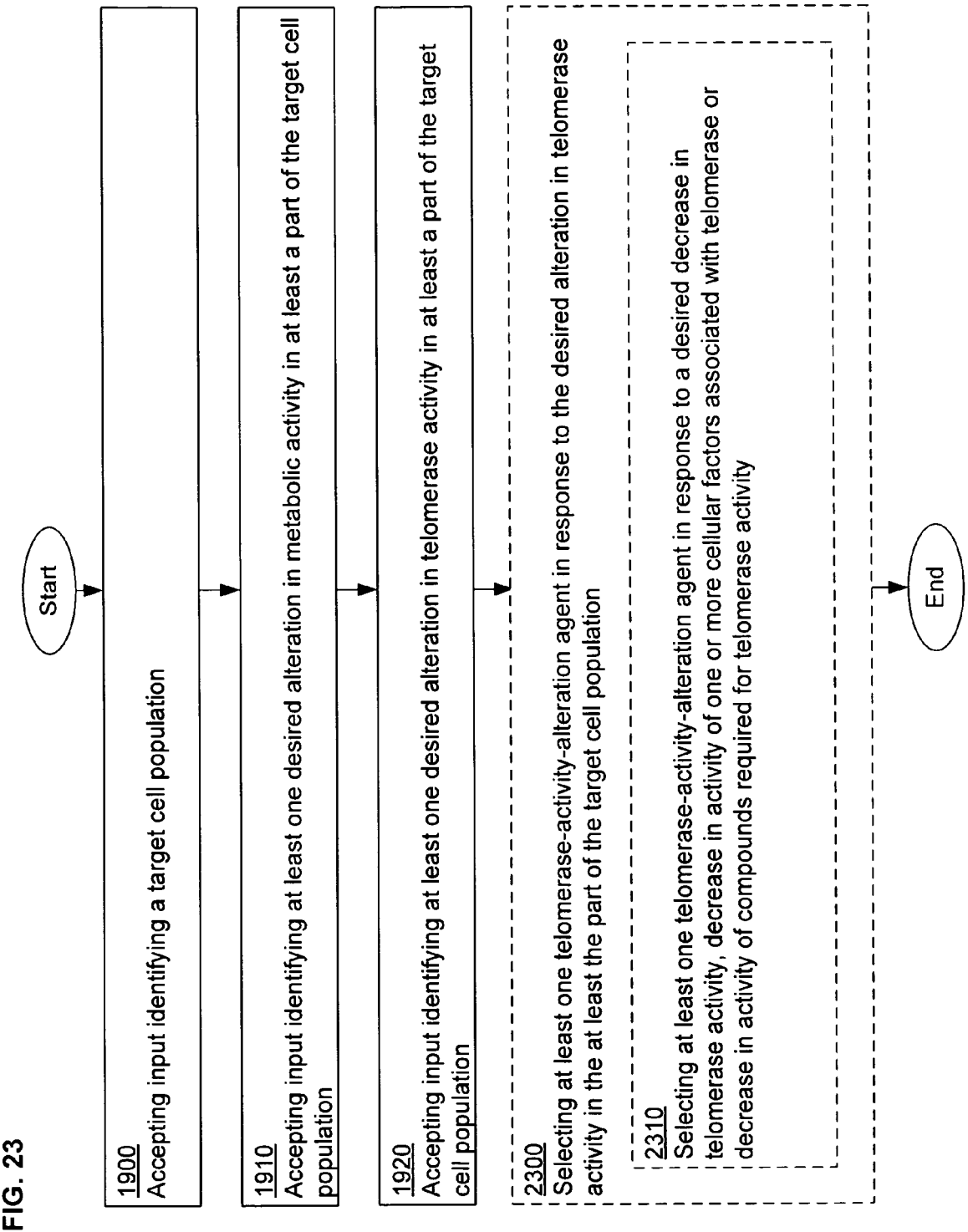
FIG. 23 is a flowchart illustrating further aspects of embodiments of the methods and systems described herein.

FIG. 23 illustrates further aspects that may be included in some embodiments. Embodiments may include selecting at least one telomerase-activity-alteration agent in response to the desired alteration in telomerase activity in the at least the part of the target cell population 2300, which may further include selecting at least one telomerase-activity-alteration agent in response to the desired alteration in telomerase activity in the at least the part of the target cell population 2310. An alteration in telomerase activity includes alterations in the active telomerase complex such as altered functionality of components or altered concentration of components, as well as alterations in the availability of components or co-factors required for telomerase activity. For example, alterations in telomerase activity may include: reductions or increases in the subunit components of a telomerase functional complex; alterations in nucleotide sequence, protein sequence, form or assembly of telomerase subunits; altered concentrations of molecules involved in telomerase activity; and altered concentrations of inhibitors of telomerase activity.

Figure 24:
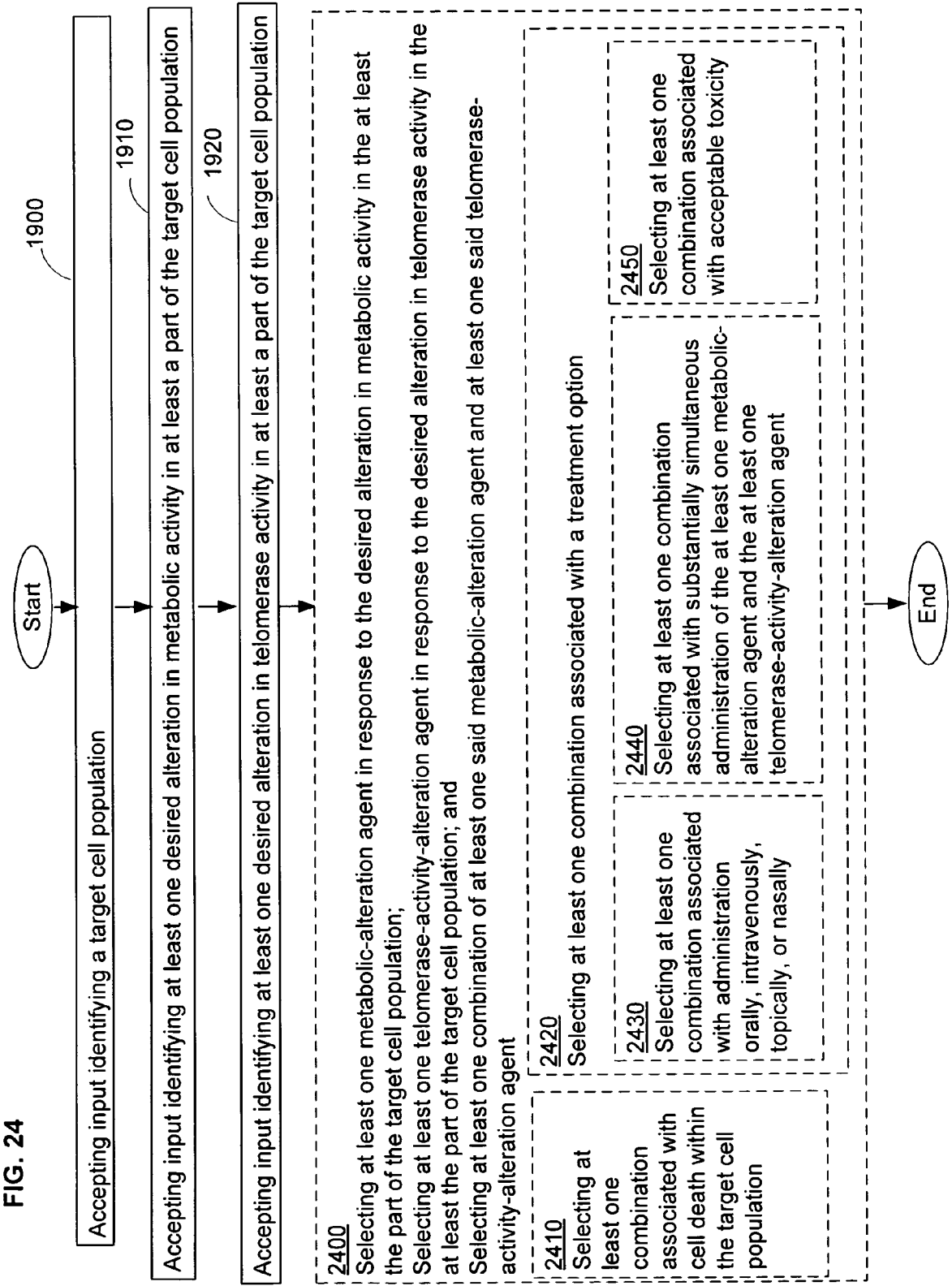
FIG. 24 is a flowchart illustrating further aspects of embodiments of the methods and systems described herein.

FIG. 24 illustrates still further aspects that may be included in some embodiments. Embodiments may include selecting at least one metabolic-alteration agent in response to the desired alteration in metabolic activity in the at least the part of the target cell population; selecting at least one telomerase-activity-alteration agent in response to the desired alteration in telomerase activity in the at least the part of the target cell population; and selecting at least one combination of at least one said metabolic-alteration agent and at least one said telomerase-activity-alteration agent 2400. As used herein, selecting at least one combination of at least one said metabolic-alteration agent and at least one said telomerase-activity-alteration agent includes selections of a combination of the agents, selected on any basis or randomly. Some aspects of selecting at least one metabolic-alteration agent in response to the desired alteration in metabolic activity in the at least the part of the target cell population; selecting at least one telomerase-activity-alteration agent in response to the desired alteration in telomerase activity in the at least the part of the target cell population; and selecting at least one combination of at least one said metabolic-alteration agent and at least one said telomerase-activity-alteration agent 2400 may further include selecting at least one combination associated with cell death within the target cell population 2410. A combination may be associated with cell death, including, for example, directly associated with cell death in a causal relationship, associated with an increase in cell death, associated with a decrease in cell death, and/or associated with cell death indirectly through one or a series of other factors.

As also illustrated in FIG. 24, some aspects may include selecting at least one metabolic-alteration agent in response to the desired alteration in metabolic activity in the at least the part of the target cell population; selecting at least one telomerase-activity-alteration agent in response to the desired alteration in telomerase activity in the at least the part of the target cell population; and selecting at least one combination of at least one said metabolic-alteration agent and at least one said telomerase-activity-alteration agent 2400, and may further include selecting at least one combination associated with a treatment option 2420. As used herein, selecting at least one combination associated with a treatment option includes, for example, selecting at least one combination including: potential treatment options, previously recognized treatment options, treatment options similar to a previously recognized treatment, or treatment options in a related compound group to a previously recognized treatments. As used herein, "treatment option" includes any combination of agents that may potentially be used as a treatment for any disease or condition in any organism, including humans and/or non-human animals and/or plants. A treatment option may be associated with administration in a given manner. In some aspects, selecting at least one combination associated with a treatment option 2420 may further include selecting at least one combination associated with administration orally, intravenously, topically, or nasally 2430. In some aspects, selecting at least one combination associated with a treatment option 2420 may further include one or more instructions for selecting at least one combination associated with substantially simultaneous administration of the at least one metabolic-alteration agent and the at least one telomerase-activity-alteration agent 2440.

One or more instructions for selecting at least one combination associated with a treatment option 2420 may further include one or more instructions for selecting at least one combination associated with acceptable toxicity 2450. As a further example, selecting at least one combination associated with a treatment option may include selecting at least one combination associated with acceptable toxicity. As used herein, acceptable toxicity includes any toxicity that is associated with being acceptable in a particular embodiment, and may include, for example: acceptable toxicity for a particular patient or class of patients such as cancer patients; acceptable toxicity in combination with other therapies; acceptable toxicity to a given group of cells; acceptable toxicity to a given organ; or acceptable toxicity to a given level, for example LD50, dermal or inhalation testing levels.

Figure 25:
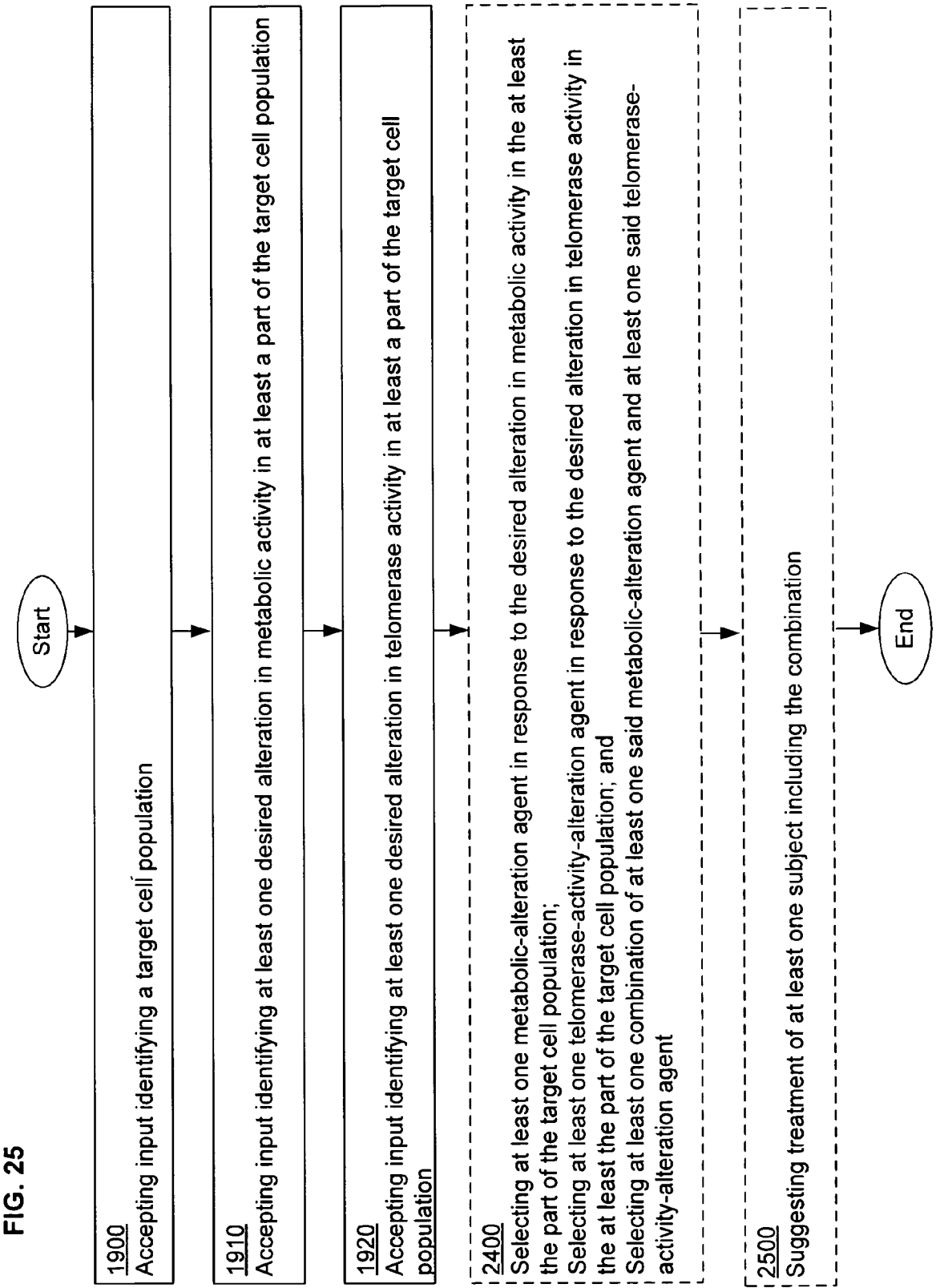
FIG. 25 is a flowchart illustrating further aspects of embodiments of the methods and systems described herein.

FIG. 25 illustrates aspects that may be included in some embodiments. As described above, aspects may include one or more instructions for selecting at least one metabolic-alteration agent in response to the desired alteration in metabolic activity in the at least the part of the target cell population; one or more instructions for selecting at least one telomerase-activity-alteration agent in response to the desired alteration in telomerase activity in the at least the part of the target cell population; and selecting at least one combination of at least one said metabolic-alteration agent and at least one said telomerase-activity-alteration agent 2400. Aspects may also include one or more instructions for suggesting treatment of at least one subject including the combination 2500. As illustrated in FIG. 18, suggesting treatment of at least one subject including the combination 2500 may be implemented by means of a user interface.

Figure 26:
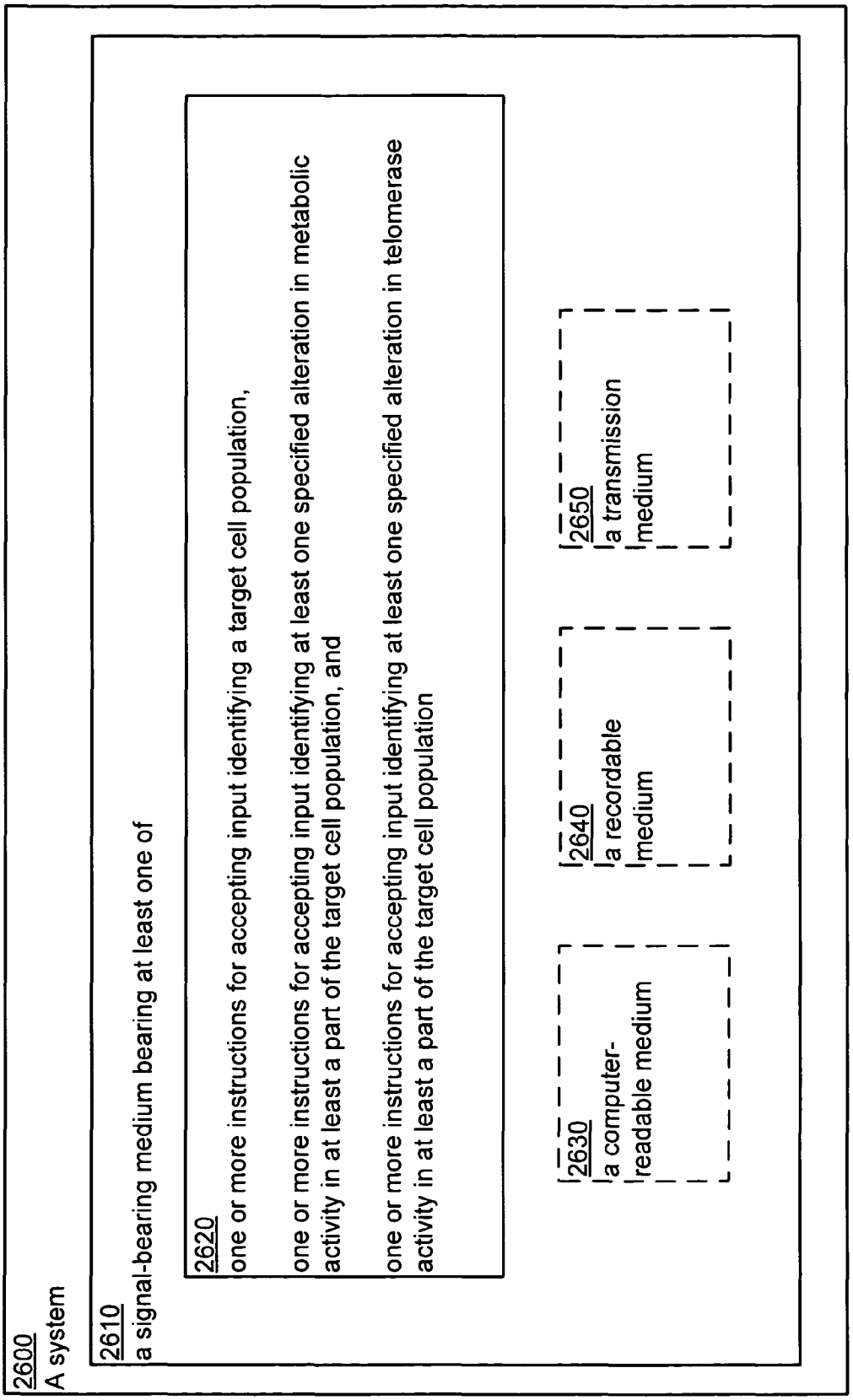
FIG. 26 is a schematic illustrating aspects of methods and systems described herein.

FIG. 26 illustrates aspects of a system 2600. An embodiment of the system 2600 is provided including a signal-bearing medium 2610 bearing at least one of one or more instructions for accepting input identifying a target cell population, one or more instructions for accepting input identifying at least one specified alteration in metabolic activity in at least a part of the target cell population; and one or more instructions for accepting input identifying at least one specified alteration in telomerase activity in at least a part of the target cell population 2620. The one or more instructions may be, for example, computer executable and/or logic-implemented instructions. In some embodiments, the signal-bearing medium 2610 may include a computer-readable medium 2630. In some embodiments, the signal bearing medium 2610 may include a recordable medium 2640. In some embodiments, the signal bearing medium 2610 may include a transmission medium 2650.

Figure 27:
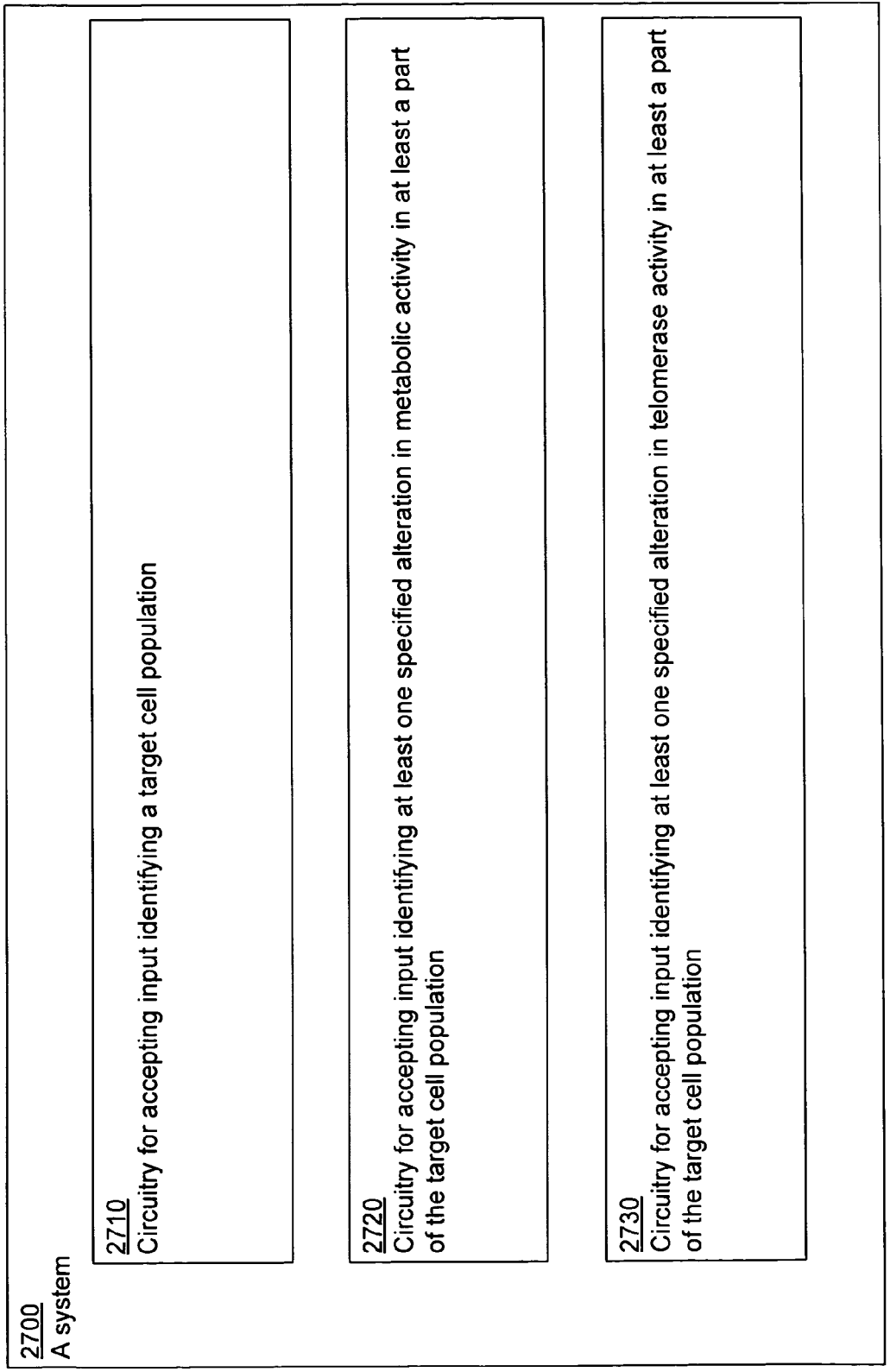
FIG. 27 is a schematic illustrating aspects of methods and systems described herein.

FIG. 27 illustrates aspects of a system 2700. An embodiment of the system 2700 is provided including: circuitry for accepting input identifying a target cell population 2710; circuitry for accepting input identifying at least one specified alteration in metabolic activity in at least a part of the target cell population 2720; and circuitry for accepting input identifying at least one specified alteration in telomerase activity in at least a part of the target cell population 2730.

Other aspects of systems described herein include means for accepting input identifying a target cell population, means for accepting input identifying at least one specified alteration in metabolic activity in at least a part of the target cell population, and means for accepting input identifying at least one specified alteration in telomerase activity in at least a part of the target cell population. Means may include software, firmware or hardware.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A computer-implemented method comprising:
   accepting, in a suitably programmed computing device, input identifying an epithelial target cell population;
   accepting, in a suitably programmed computing device, input identifying at least one specified alteration in metabolic activity in at least a part of the epithelial target cell population;
   accepting, in a suitably programmed computing device, input identifying at least one specified alteration in telomerase activity in at least a part of the epithelial target cell population;
   selecting at least one metabolic-alteration agent in response to the input alteration in metabolic activity in the at least the part of the epithelial target cell population;
   selecting at least one telomerase-activity-alteration agent in response to the input alteration in telomerase activity in the at least the part of the epithelial target cell population;
   selecting at least one combination of at least one said metabolic-alteration agent and at least one said telomerase-activity-alteration agent, wherein the selected at least one combination is associated with at least one treatment option and is associated with topical administration; and
   indicating, in a suitably programmed computing device, the selected at least one combination to at least one system user.

2. The method of claim 1, wherein said accepting, in a suitably programmed computing device, input identifying an epithelial target cell population comprises:
   accepting input identifying at least one melanoma cell, basal cell carcinoma cell, squamous cell carcinoma cell, wart cell, neoplastic cell, dysplastic cell, hyperplastic cell, freckle cell, or non-terminally differentiated cell.

3. The method of claim 1, wherein said accepting, in a suitably programmed computing device, input identifying an epithelial target cell population comprises:
   accepting input identifying a target cell population in situ, ex situ, in vivo, or ex vivo.

4. The method as in claim 1 wherein said accepting, in a suitably programmed computing device, input identifying at least one specified alteration in metabolic activity in at least a part of the epithelial target cell population further comprises:
   accepting input identifying mitotic acceleration, mitotic deceleration, increased differentiation, stabilized differentiation, cell growth acceleration, cell growth deceleration, cell cycle progression, or cell cycle stasis.

5. The method as in claim 1, further comprising:
   accepting input identifying one or more cellular features associated with the epithelial target cell population.

6. The method as in claim 5 wherein said accepting input identifying one or more cellular features associated with the epithelial target cell population comprises:
   accepting input identifying mitotic index, location, cell size, mass size, mutation, ploidy, or protein expression.

7. The method of claim 1, further comprising:
   selecting at least one metabolic-alteration agent in response to the specified alteration in metabolic activity in the at least the part of the epithelial target cell population.

8. The method of claim 7, wherein said selecting at least one metabolic-alteration agent in response to the specified alteration in metabolic activity in the at least the part of the epithelial target cell population further comprises:
   recalling one or more cellular feature characteristics associated with the epithelial target cell population; and
   identifying at least one agent predicted to preferentially alter metabolic activity in response to the one or more cellular feature characteristics associated with the epithelial target cell population.

9. The method as in claim 7, wherein said selecting at least one metabolic-alteration agent in response to the specified alteration in metabolic activity in the at least the part of the epithelial target cell population further comprises:
   identifying at least one agent associated with mitotic acceleration.

10. The method as in claim 7, wherein said selecting at least one metabolic-alteration agent in response to the specified alteration in metabolic activity in the at least the part of the epithelial target cell population further comprises:
    identifying at least one metabolic-alteration agent in response to a desired alteration in metabolic activity related to differentiation, mitosis, cell growth, or cell cycle activity.

11. The method as in claim 7, wherein said selecting at least one metabolic-alteration agent in response to the specified alteration in metabolic activity in the at least the part of the epithelial target cell population further comprises:
    identifying at least one agent that includes all trans retinoic acid in response to a desired alteration in metabolic activity related to mitosis.

12. The method as in claim 7, wherein said selecting at least one metabolic-alteration agent in response to the specified alteration in metabolic activity in the at least the part of the epithelial target cell population further comprises:
    identifying at least one agent associated with a tumor necrosis factor (TNF) alpha related signaling pathway.

13. The method as in claim 7, wherein said selecting at least one metabolic-alteration agent in response to the specified alteration in metabolic activity in the at least the part of the epithelial target cell population further comprises:

identifying at least one agent associated with a Sonic Hedgehog related signaling pathway.

14. The method as in claim 7, wherein said selecting at least one metabolic-alteration agent in response to the specified alteration in metabolic activity in the at least the part of the epithelial target cell population further comprises:
identifying at least one agent associated with upregulation of endogenous p53 in at least one epithelial cell.

15. The method of claim 1, further comprising:
selecting at least one telomerase-activity-alteration agent in response to the specified alteration in telomerase activity in the at least the part of the epithelial target cell population.

16. The method as in claim 15, wherein said selecting at least one telomerase-activity-alteration agent in response to the specified alteration in telomerase activity in the at least the part of the epithelial target cell population further comprises:
selecting at least one telomerase-activity-alteration agent in response to a desired decrease in telomerase activity, decrease in activity of one or more cellular factors associated with telomerase or decrease in activity of one or more compounds required for telomerase activity.

17. The method as in claim 1, wherein selecting at least one combination of at least one said metabolic-alteration agent and at least one said telomerase-activity-alteration agent comprises:
selecting at least one combination associated with cell death within the epithelial target cell population.

18. The method as in claim 1, wherein the selected at least one combination that is associated with a treatment option comprises:
selecting at least one combination associated with substantially simultaneous administration of the at least one metabolic-alteration agent and the at least one telomerase-activity-alteration agent.

19. The method as in claim 1, wherein the selected at least one combination that is associated with a treatment option comprises:
selecting at least one combination associated with acceptable toxicity.

20. A system comprising:
a recordable type, computer readable medium, bearing:
one or more instructions for accepting input identifying an epithelial target cell population, comprises:
one or more instructions for accepting input identifying at least one specified alteration in metabolic activity in at least a part of the epithelial target cell population,
one or more instructions for accepting input identifying at least one specified alteration in telomerase activity in at least a part of the epithelial target cell population;
one or more instructions for selecting at least one metabolic-alteration agent in response to the input alteration in metabolic activity in the at least the part of the epithelial target cell population;
one or more instructions for selecting at least one telomerase-activity-alteration agent in response to the input alteration in telomerase activity in the at least the part of the epithelial target cell population; and
one or more instructions for selecting at least one combination of at least one said metabolic-alteration agent and at least one said telomerase-activity-alteration agent, wherein the selected at least one combination is associated with at least one treatment option and is associated with topical administration; and
one or more instructions for indicating the selected at least one combination to at least one system user.

21. The system as in claim 20, wherein said one or more instructions for accepting input identifying an epithelial target cell population comprises:
one or more instructions for accepting input identifying at least one melanoma cell, basal cell carcinoma cell, squamous cell carcinoma cell, wart cell, neoplastic cell, dysplastic cell, hyperplastic cell, freckle cell, or non-terminally differentiated cell.

22. The system as in claim 20, wherein the one or more instructions for accepting input identifying an epithelial target cell population comprises:
one or more instructions for accepting input identifying an epithelial target cell population in situ, ex situ, in vivo, or ex vivo.

23. The system as in claim 20, wherein the one or more instructions for accepting input identifying at least one specified alteration in metabolic activity in at least a part of the epithelial target cell population further comprises:
one or more instructions for accepting input identifying mitotic acceleration, mitotic deceleration, increased differentiation, stabilized differentiation, cell growth acceleration, cell growth deceleration, cell cycle progression, or cell cycle stasis.

24. The system as in claim 20, comprising:
one or more instructions for accepting input identifying one or more cellular features associated with the epithelial target cell population.

25. The system as in claim 24, wherein the one or more instructions for accepting input identifying one or more cellular features associated with the epithelial target cell population comprises:
one or more instructions for accepting input identifying mitotic index, location, cell size, mass size, mutation, ploidy, or protein expression.

26. The system as in claim 20, further comprising:
one or more instructions for selecting at least one metabolic-alteration agent in response to the specified alteration in metabolic activity in the at least the part of the epithelial target cell population.

27. The system as in claim 26 wherein said one or more instructions for selecting at least one metabolic-alteration agent in response to the specified alteration in metabolic activity in the at least the part of the epithelial target cell population further comprises:
one or more instructions for recalling one or more cellular feature characteristics associated with the epithelial target cell population; and
one or more instructions for identifying at least one agent predicted to preferentially alter metabolic activity in response to the one or more cellular feature characteristics associated with the epithelial target cell population.

28. The system as in claim 26 wherein said one or more instructions for selecting at least one metabolic-alteration agent in response to the specified alteration in metabolic activity in the at least the part of the epithelial target cell population further comprises:
one or more instructions for identifying at least one agent associated with mitotic acceleration.

29. The system as in claim 26 wherein said one or more instructions for selecting at least one metabolic-alteration agent in response to the specified alteration in metabolic activity in the at least the part of the epithelial target cell population further comprises:
one or more instructions for identifying at least one metabolic-alteration agent in response to a desired alteration in metabolic activity related to differentiation, mitosis, cell growth, or cell cycle activity.

30. The system as in claim 26 wherein said one or more instructions for selecting at least one metabolic-alteration agent in response to the specified alteration in metabolic activity in the at least the part of the epithelial target cell population further comprises:
one or more instructions for identifying at least one agent that includes all trans retinoic acid in response to a desired alteration in metabolic activity related to mitosis.

31. The system as in claim 26 wherein said one or more instructions for selecting at least one metabolic-alteration agent in response to the specified alteration in metabolic activity in the at least the part of the epithelial target cell population further comprises:
one or more instructions for identifying at least one agent associated with a tumor necrosis factor (TNF) alpha related signaling pathway.

32. The system as in claim 26 wherein said one or more instructions for selecting at least one metabolic-alteration agent in response to the specified alteration in metabolic activity in the at least the part of the epithelial target cell population further comprises:
one or more instructions for identifying at least one agent associated with a Sonic Hedgehog related signaling pathway.

33. The system as in claim 26 wherein said one or more instructions for selecting at least one metabolic-alteration agent in response to the specified alteration in metabolic activity in the at least the part of the epithelial target cell population further comprises:
one or more instructions for identifying at least one agent associated with upregulation of endogenous p53 in at least one epithelial cell.

34. The system as in claim 20 further comprising:
one or more instructions for selecting at least one telomerase-activity-alteration agent in response to the specified alteration in telomerase activity in the at least the part of the epithelial target cell population.

35. The system as in claim 34 wherein the one or more instructions for selecting at least one telomerase-activity-alteration agent in response to the specified alteration in telomerase activity in the at least the part of the epithelial target cell population further comprises:
one or more instructions for selecting at least one telomerase-activity-alteration agent in response to a desired decrease in telomerase activity, decrease in activity of one or more cellular factors associated with telomerase or decrease in activity of one or more compounds required for telomerase activity.

36. The system as in claim 20 wherein the one or more instructions for selecting at least one combination of at least one said metabolic-alteration agent and at least one said telomerase-activity-alteration agent comprises:
one or more instructions for selecting at least one combination associated with cell death within the epithelial target cell population.

37. The system as in claim 20, wherein the selected at least one combination that is associated with a treatment option comprises:
one or more instructions for selecting at least one combination associated with substantially simultaneous administration of the at least one metabolic-alteration agent and the at least one telomerase-activity-alteration agent.

38. The system as in claim 20, wherein the selected at least one combination that is associated with a treatment option comprises:
one or more instructions for selecting at least one combination associated with acceptable toxicity.

39. A system comprising:
circuitry for accepting input identifying an epithelial target cell population;
circuitry for accepting input identifying at least one specified alteration in metabolic activity in at least a part of the epithelial target cell population; and
circuitry for accepting input identifying at least one specified alteration in telomerase activity in at least a part of the epithelial target cell population;
circuitry for selecting at least one metabolic-alteration agent in response to the input alteration in metabolic activity in the at least the part of the epithelial target cell population;
circuitry for selecting at least one telomerase-activity-alteration agent in response to the input alteration in telomerase activity in the at least the part of the epithelial target cell population;
circuitry for selecting at least one combination of at least one said metabolic-alteration agent and at least one said telomerase-activity-alteration agent, wherein the selected at least one combination is associated with at least one treatment option and is associated with topical administration; and
circuitry for indicating the selected at least one combination to at least one system user.

40. A system comprising:
means for accepting input identifying an epithelial target cell population;
means for accepting input identifying at least one specified alteration in metabolic activity in at least a part of the epithelial target cell population; and
means for accepting input identifying at least one specified alteration in telomerase activity in at least a part of the epithelial target cell population;
means for selecting at least one metabolic-alteration agent in response to the input alteration in metabolic activity in the at least the part of the epithelial target cell population;
means for selecting at least one telomerase-activity-alteration agent in response to the input alteration in telomerase activity in the at least the part of the epithelial target cell population;
means for selecting at least one combination of at least one said metabolic-alteration agent and at least one said telomerase-activity-alteration agent, wherein the selected at least one combination is associated with at least one treatment option and is associated with topical administration; and
means for indicating the selected at least one combination to at least one system user.

* * * * *

UNITED STATES PATENT AND TRADEMARK OFFICE
CERTIFICATE OF CORRECTION

| | |
|---|---|
| PATENT NO. | : 7,894,994 B2 |
| APPLICATION NO. | : 11/510123 |
| DATED | : February 22, 2011 |
| INVENTOR(S) | : Roderick A. Hyde et al. |

It is certified that error appears in the above-identified patent and that said Letters Patent is hereby corrected as shown below:

Column 15, Line 45, Claim 20: "population," should be --population--

Column 16, Lines 12-13, Claim 22: "one or more instructions for accepting input identifying an epithelial target cell population" should be --one or more instructions for identifying the epithelial target cell population--

Signed and Sealed this
Twenty-fourth Day of May, 2011

David J. Kappos
*Director of the United States Patent and Trademark Office*